(12) United States Patent
Weissbach et al.

(10) Patent No.: US 8,765,808 B2
(45) Date of Patent: Jul. 1, 2014

(54) TREATMENT OR PREVENTION OF CANCER AND PRECANCEROUS DISORDERS

(75) Inventors: Herbert Weissbach, Boynton Beach, FL (US); Lionel Resnick, Boca Raton, FL (US); David Binninger, Delray Beach, FL (US)

(73) Assignee: CHS Pharma, Inc., Jupiter, FL (US)

( * ) Notice: Subject to any disclaimer, the term of this patent is extended or adjusted under 35 U.S.C. 154(b) by 2063 days.

(21) Appl. No.: 11/925,283

(22) Filed: Oct. 26, 2007

(65) Prior Publication Data

US 2008/0119559 A1    May 22, 2008

Related U.S. Application Data

(63) Continuation-in-part of application No. 11/388,248, filed on Mar. 23, 2006, now Pat. No. 8,258,181.

(60) Provisional application No. 60/664,383, filed on Mar. 23, 2005.

(51) Int. Cl.
*A61K 31/255* (2006.01)
*A61K 33/40* (2006.01)

(52) U.S. Cl.
USPC ........... 514/518; 424/616; 514/18.7; 514/516

(58) Field of Classification Search
USPC ..................... 424/616; 514/18.7, 516, 518
See application file for complete search history.

(56) References Cited

U.S. PATENT DOCUMENTS

| 4,732,864 | A |   | 3/1988  | Tolman |     |
|-----------|---|---|---------|--------|-----|
| 5,204,116 | A | * | 4/1993  | Edgren et al. | 424/473 |
| 5,370,870 | A |   | 12/1994 | Wong |     |
| 5,563,132 | A | * | 10/1996 | Bodaness | 514/185 |
| 2003/0143165 | A1 |   | 7/2003 | Evans et al. |     |
| 2004/0137077 | A1 |   | 7/2004 | Ancira et al. |     |
| 2004/0234625 | A1 |   | 11/2004 | Burstein |     |

FOREIGN PATENT DOCUMENTS

| WO | 00/50448 A1 | 8/2000 |
| WO | 2006/102439 A2 | 9/2006 |

OTHER PUBLICATIONS

Athar et al., "Photoprotective effects of sulindac against ultraviolet B-induced phototoxicity in the skin of SKH-1 hairless mice", Jan. 10, 2004, Toxicology and Applied Pharmacology, vol. 195 issue 3, pp. 370-378.*
Etienne et al., "Reduction of Sulindac to its active metabolite, sulindac sulfide: assay and role of the methionine sulfoxide reductase system", 2003, Biochemical and Biophysical Research Communications, vol. 312, pp. 1005-1010.*
Berman et al., Sulindac Enhances Tumor Necrosis Factor-α-mediated Apoptosis of Lung Cancer Cell Lines by Inhibition of Nuclear Factor-κB, Published Feb. 2002, Clinical Cancer Research, vol. 8, pp. 354-360.*
Scherck et al., Nuclear Factor KB: An Oxidative Stress-Responsive Transcription Factor of Eukaryotic Cells (A Review), Published 1992, Free Radical Research, vol. 17 No. 4, abstract.*
O'Connor Robert et al, "Increased anti-tumour efficacy of doxorubicin when combined with sulindac in a xenograft model of an MRP-1-positive human lung cancer": Anticancer Research, The National Institute for Cellular Biotechnology, Ireland, (2004), vol. 24, pp. 457-464, XP008125995.
Kim Hak Ryul et al, "Combination of arsenic trioxide with sulindac augments cell death and induced apoptosis via activation of caspase cascade in NCI-H157 human lung carcinoma cells": Proceedings of the American Association for Cancer Research; Rep. of Korea, (2004), vol. 45, p. 1227, XP008125990.
Matsubara, J., Experientia Supplementum, 1987, vol. 52, pp. 603-612, especially abstract, p. 610.
Clinical cancer research abstract. AACR special Conference, Fig 5, (2006) Combination therapy-medicated oxidative DNA damage in DLD-1 cells, http://clincancerres.aacrjournals.org/content/12/21/6532.full, retrieved Jun. 20, 2011.
Supplementary European Search Report; EP 06 74 8561, dated Sep. 1, 2010.

* cited by examiner

*Primary Examiner* — Ali Soroush
(74) *Attorney, Agent, or Firm* — CHS Pharma, Inc.; Stanley A. Kim

(57) ABSTRACT

The NSAID, sulindac and/or its metabolites and derivatives, in combination with hydrogen peroxide or another oxidizing agent, such as arsenic trioxide that generates reactive oxygen species (ROS), significantly enhances the killing of cancer cells. This effect occurs at concentrations of each compound that individually have little or no activity directed against cancer cells. A skin cream has been developed and used to treat skin cancer and precancerous skin growths that effectively removes the lesions with no effect on surrounding normal skin.

7 Claims, 26 Drawing Sheets

A.

B.

22  28 Minutes

TREATMENT OR PREVENTION OF CANCER AND PRECANCEROUS DISORDERS

CROSS REFERENCE TO PRIOR APPLICATIONS

The present application is a continuation-in-part prosecution of U.S. application Ser. No. 11/388,248 filed Mar. 23, 2006 now U.S. Pat. No. 8,258,181 which claims the priority of U.S. provisional patent application No. 60/664,383, entitled "TREATMENT OR PREVENTION OF CANCER AND PRECANCEROUS DISORDERS," filed Mar. 23, 2005. The foregoing are incorporated herein by reference in their entirety.

FIELD OF THE INVENTION

Compositions for treating cancer and methods of treating thereof. In particular, sulindac and/or its metabolites and derivatives, in either R- or S-epimeric form in combination with hydrogen peroxide or another oxidizing agent, such as arsenic trioxide that generates reactive oxygen species (ROS), significantly enhances the killing of cancer cells.

BACKGROUND OF THE INVENTION

Skin cancer is the most common form of cancer seen in the world. The two most common types of non-melanoma skin cancer include basal cell carcinoma (BCC) and squamous cell carcinoma (SCC). One in five Americans will develop some form of skin cancer at some point in their lives, and it is estimated that over one million Americans will develop skin cancer each year.

Sun exposure has been implicated in the etiology of BCC and SCC. The epidemic rise in the rate of these cancers is directly related to increases in our population's outdoor activities and the desire for a "tanned" skin appearance. Premalignant actinic keratoses are common skin growths induced by solar exposure that have the potential for developing into SCC in upwards of 20% of cases. They often appear on the skin years before the development of cutaneous carcinomas.

It is considered a standard of care to remove as many skin cancers and actinic keratoses as possible with the least amount of discomfort, inconvenience and trauma (morbidity), for the patient. Destruction using liquid nitrogen or electrodessication and curettage are effective in removing a majority of skin cancers and actinic keratoses. However, these treatments may not be practical for certain skin cancers located on the face and extremities. Surgical removal of skin cancers and actinic keratoses is not always possible or desirable. Surgery is not practical when many small actinic keratoses are present, and the scarring produced by surgery is generally unacceptable for exposed, relatively visible areas of the skin. Furthermore, it is believed that, in the early stages of their development, many skin cancers and actinic keratoses are so small that it would be difficult or impossible to remove surgically because they are not visible to the eye. Surgery, while necessary for the welfare of the patient, may place the patient at risk and ultimately jeopardize their health if the cancer is located adjacent to certain vital areas, such as the eye. In addition, surgery may lead to a poor cosmetic effect and leave the patient visibly deformed.

Topically applied, chemical agents such as 5-flurouracil (5-FU), masoprocol, imiquimod, and diclofenac have been approved to eradicate actinic keratoses. While 5-FU has demonstrated efficacy for this purpose, it has been found to cause pain, itching, skin inflammation, ulceration and cosmetic disfigurement often so severe that patients hide at home and stop using it, thus making its therapeutic use unacceptable to many individuals. These effects also preclude the use of 5-FU over large areas of the skin to treat incipient and/or microscopic actinic keratoses. Masoprocol was removed from the US market in 1996 after it was found to have a high incidence of contact sensitivity and allergic reactions. Imiquimod has a relatively good cosmetic effect when treating actinic keratoses but is very expensive for use in large areas of the skin and its packaging in pouches has not been well received by many patients. The Food and Drug Administration recently approved imiquimod for the treatment of BC. However, this indication excludes treatment of BCC that occurs on the face. Diclofenac is a non-steroidal anti-inflammatory drug (NSAID) used to treat actinic keratoses. It has very modest effects and removal of the actinic keratoses may not be evident until months after treatment ends. However, it causes less irritation than 5-FU and imiquimod and may be useful for some people.

There are several newer therapeutic approaches directed against actinic keratoses that are in clinical trials such as the use of photodynamic therapy (PDT) with aminolevulinic acid. This therapy is a two-step treatment administered over a two-day period. First, the aminolevulinic acid is place over the lesion and on the next day, a blue light is used to activate the drug. However, this treatment is expensive, needs to be done at the doctor's office, is used only for thin lesions, and is not very effective.

There is thus a need in the art to develop, safe, effective and specificity of killing of abnormal cell, that is also cost effective.

SUMMARY

We have discovered that the NSAID, sulindac and/or its metabolites and derivatives, in combination with hydrogen peroxide or another oxidizing agent, such as arsenic trioxide that generates reactive oxygen species (ROS), significantly enhances the killing of cancer cells. This effect occurs at concentrations of each compound that individually have little or no activity directed against cancer cells. A skin cream has been developed and used to treat skin cancer and precancerous skin growths that effectively removes the lesions with no effect on surrounding normal skin.

We have shown that four tumor cell lines—two derived from skin (SCC and melanoma), and colon and lung cell lines—exhibit markedly increased sensitivities to killing by oxidative stress when pretreated with sulindac. Similar effects were observed with two different forms of direct oxidative stress—hydrogen peroxide and tert-butyl hydroperoxide (TBHP) or the use of arsenic trioxide, a compound that generates the production of ROS. This effect occurs at concentrations of each compound that individually have little or no activity directed against cancer cells. The killing effect was not observed when using normal human skin, colon, or lung cells. In contrast, the normal cells exhibited a protective effect with the combination of sulindac and peroxide at the lower concentrations of peroxide. Sulindac metabolites (sulindac sulfide in some instances and sulindac sulfone), and a sulindac derivative (sulindac methionine sulfoxide) also had enhanced killing effects of cancer cells when exposed to peroxide. Experiments with four other NSAIDS, (acetylsalicylic acid, ibuprofen, diclofenac sodium, and celecoxib) indicated that none were effective in producing the enhanced killing effects after exposure to the oxidating agents. The mechanism of action of this therapy may be associated with a selective increase in the ROS levels in cancer cells as opposed to normal cells which, in general, has an opposite effect leading to no change or a lowering in the levels of ROS. Thus, this drug combination can be useful for the treatment of cancer and precancerous conditions without the killing of normal cells.

When such combinations of sulindac and hydrogen peroxide are formulated and applied topically using an inert vehicle to the area of the skin exhibiting the precancerous or cancerous condition, for example, an actinic keratosis, SCC, or a BCC, the lesions over a period of several weeks completely resolve and disappear. There was minimal redness, swelling, and peeling with no itching, burning, sores or blisters that developed. An enhanced yellowish color was visibly present on the skin condition being treated prior to its destruction. This yellow color may be an indication of patient compliance for the accurate documentation of its clinical use by the patient. Sulindac or peroxide when applied alone to the skin condition had no effect on the precancerous or cancerous growth.

It will thus be appreciated that there is a need for topically active agents which are effective in removing actinic keratoses, BCC and SCC. These agents should attempt to avoid the undesirable side effects of current treatments, shorten the time for removal and healing of the lesions, lower the expense of the therapy, and increase its compliance for use by the patient.

In a preferred embodiment, a pharmaceutical composition comprises sulindac, sulindac metabolites, sulindac derivatives and an oxidating agent. Preferably, the sulindac metabolite comprises sulindac sulfide or sulindac sulfone. Preferably, the sulindac derivative is sulindac methionine sulfoxide.

In another preferred embodiment, the sulindac comprises R- and S-epimers of sulindac. Preferably, the sulindac is an R-epimer. We have discovered that the R-epimer of sulindac can retain its cancer killing effects. We have also found that in normal cells, but not cancer cells, the R-epimer of sulindac is not efficiently converted to the sulfide, the active COX inhibitor. Since COX inhibitors produce serious toxicity, it is expected that the R-epimer of sulindac can be a potentially superior therapeutic agent because it would have a lower toxicity profile in normal cells.

In another preferred embodiment, the oxidating agent comprises at least one of: peroxides, nitrates, nitrites, perchlorates, chlorates, chlorites, hypochlorite, dichromates, permanganates, and persulfates, bromine, arsenic trioxide, retinoic acid (and its derivatives), K antimonyl tartrate, doxorubicin, imexon, and bortezomib, hydrogen peroxide; inorganic peroxides, sodium peroxyborate tetrahydrate (sodium perborate tetrahydrate) calcium peroxide; peroxide complexes, urea hydrogen peroxide; superoxide salts, sodium superoxide; superoxide free radical ($O_2^*$) dismutates; organic peroxides, hydroperoxides (ROOH), lipid hydroperoxides, artemisinin and derivatives thereof; 1-Hydroperoxycyclohexyl-1-hydroxy cyclohexyl peroxide, tert-Butyl hydroperoxide; fatty acid hydroperoxides, linolenic acid hydroperoxide, arachidonic acid hydroperoxide, docosahexaenoic acid hydroperoxide, cholesterol hydroperoxide, cholesteryl linoleate hydroperoxide, trilinolein hydroperoxide, phosphatidylcholine hydroperoxide, phosphatidylethanolamine hydroperoxide; 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl)dioxy)-cyclohexanol; hydrogen peroxide, compounds containing a peroxy (peroxo) —O—O— moiety, superoxides, peroxide precursor compounds; endoperoxides, diacyl peroxides, ketone peroxides, peroxydicarbonates, peroxyesters, dialkyl peroxides, peroxyketals, and peroxyacids. Preferably, the oxidating agent is hydrogen peroxide, and/or tert-butyl hydroperoxide (TBHP), and/or arsenic trioxide.

In another preferred embodiment, the oxidizing agent is hydrogen peroxide in a concentration is in a range of about 1% to 50% by weight.

In another preferred embodiment, the sulindac concentration is in range from about 1% to 50% by weight.

In yet another embodiment, the oxidizing agent is arsenic trioxide in a concentration in a range of about 1% to 50% by weight.

In another preferred embodiment, a topical pharmaceutical composition comprises a 5% sulindac gel and an oxidizing agent. Preferably, the 5% sulindac gel comprises: 71.08% deionized water; 12.00% SD Alcohol 40; 10% KOH; 5% Sulindac; 1% Hydroxy methyl cellulose; 0.50% Xantham gum; 0.20% GLYDANT PLUS (DMDMH&IPBC); 0.20% Citric Acid; and 0.02% disodium EDTA.

In other preferred embodiments, the sulindac gel is 10% sulindac, 15% sulindac, 20% sulindac, 50% sulindac.

In another preferred embodiment, a method of treating an abnormal cell, said method comprising administering to an abnormal cell a pharmaceutical composition comprising sulindac, or sulindac metabolites, or sulindac derivatives or combinations thereof, and an oxidating agent, thereby treating an abnormal cell. Preferably, the sulindac metabolite comprises sulindac sulfide or sulindac sulfone.

In another preferred embodiment, the oxidating agent comprises at least one of: peroxides, nitrates, nitrites, perchlorates, chlorates, chlorites, hypochlorite, dichromates, permanganates, and persulfates, bromine, arsenic trioxide, retinoic acid (and its derivatives), K antimonyl tartrate, doxorubicin, imexon, and bortezomib, hydrogen peroxide; inorganic peroxides, sodium peroxyborate tetrahydrate (sodium perborate tetrahydrate) calcium peroxide; peroxide complexes, urea hydrogen peroxide; superoxide salts, sodium superoxide; superoxide free radical ($O_2^*$) dismutates; organic peroxides, hydroperoxides (ROOH), lipid hydroperoxides, artemisinin and derivatives thereof; 1-Hydroperoxycyclohexyl-1-hydroxy cyclohexyl peroxide, tert-Butyl hydroperoxide; fatty acid hydroperoxides, linolenic acid hydroperoxide, arachidonic acid hydroperoxide, docosahexaenoic acid hydroperoxide, cholesterol hydroperoxide, cholesteryl linoleate hydroperoxide, trilinolein hydroperoxide, phosphatidylcholine hydroperoxide, phosphatidylethanolamine hydroperoxide; 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl)dioxy)-cyclohexanol; hydrogen peroxide, compounds containing a peroxy (peroxo) —O—O— moiety, superoxides, peroxide precursor compounds; endoperoxides, diacyl peroxides, ketone peroxides, peroxydicarbonates, peroxyesters, dialkyl peroxides, peroxyketals, and peroxyacids. Preferably, the oxidating agent is hydrogen peroxide and/or tert-butyl hydroperoxide (TBHP), and/or arsenic trioxide.

In another preferred embodiment, the oxidizing agent, hydrogen peroxide, concentration is in a range of about 1% to 50% by weight.

In another preferred embodiment, the sulindac concentration is in range from about 1% to 50% by weight.

In another preferred embodiment, the oxidizing agent, arsenic trioxide, concentration is in a range of about 1% to 50% by weight.

In another preferred embodiment, the pharmaceutical composition comprises a 5% sulindac gel and an oxidizing agent. Preferably, the 5% sulindac gel comprises: 71.08% deionized water; 12.00% SD Alcohol 40; 10% KOH; 5% Sulindac; 1% Hydroxy methyl cellulose; 0.50% Xantham gum; 0.20% GLYDANT PLUS (DMDMH&IPBC); 0.20% Citric Acid; and 0.02% disodium EDTA.

In other preferred embodiments, the sulindac gel is 10% sulindac, 15% sulindac, 20% sulindac, 50% sulindac.

In yet another embodiment, a method of treating cancer, said method comprising administering to a cancer cell a pharmaceutical composition comprising sulindac, or sulindac metabolites, or sulindac derivatives or combinations thereof, and an oxidating agent, thereby treating cancer. Sulindac, sulindac metabolites, sulindac derivatives and an oxidating agent. Preferably, the sulindac metabolite comprises sulindac sulfide or sulindac sulfone.

In another preferred embodiment, the oxidating agent comprises at least one of: peroxides, nitrates, nitrites, perchlorates, chlorates, chlorites, hypochlorite, dichromates, permanganates, and persulfates, bromine, arsenic trioxide, retinoic acid (and its derivatives), K antimonyl tartrate, doxorubicin, imexon, and bortezomib, hydrogen peroxide; inorganic peroxides, sodium peroxyborate tetrahydrate (sodium perborate tetrahydrate) calcium peroxide; peroxide complexes, urea hydrogen peroxide; superoxide salts, sodium superoxide; superoxide free radical ($O_2^*$) dismutates; organic peroxides, hydroperoxides (ROOH), lipid hydroperoxides, artemisinin and derivatives thereof; 1-Hydroperoxy-cyclohexyl-1-hydroxy cyclohexyl peroxide, tert-Butyl hydroperoxide; fatty acid hydroperoxides, linolenic acid hydroperoxide, arachidonic acid hydroperoxide, docosahexaenoic acid hydroperoxide, cholesterol hydroperoxide, cholesteryl linoleate hydroperoxide, trilinolein hydroperoxide, phosphatidylcholine hydroperoxide, phosphatidylethanolamine hydroperoxide; 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl) dioxy)-cyclohexanol; hydrogen peroxide, compounds containing a peroxy (peroxo) —O—O— moiety, superoxides, peroxide precursor compounds; endoperoxides, diacyl peroxides, ketone peroxides, peroxydicarbonates, peroxyesters, dialkyl peroxides, peroxyketals, and peroxyacids. Preferably, the oxidating agent is hydrogen peroxide, and/or tert-butyl hydroperoxide (TBHP), and/or arsenic trioxide.

In another preferred embodiment, the oxidizing agent is hydrogen peroxide in a concentration is in a range of about 1% to 50% by weight.

In another preferred embodiment, the sulindac concentration is in range from about 1% to 50% by weight.

In yet another embodiment, the oxidizing agent is arsenic trioxide in a concentration in a range of about 1% to 50% by weight.

In another preferred embodiment, a topical pharmaceutical composition comprises a 5% sulindac gel and an oxidizing agent. Preferably, the 5% sulindac gel comprises: 71.08% deionized water; 12.00% SD Alcohol 40; 10% KOH; 5% Sulindac; 1% Hydroxy methyl cellulose; 0.50% Xantham gum; 0.20% GLYDANT PLUS (DMDMH&IPBC); 0.20% Citric Acid; and 0.02% disodium EDTA.

In other preferred embodiments, the sulindac gel is 10% sulindac, 15% sulindac, 20% sulindac, 50% sulindac. The oxidizing agent comprises between about 1% to 50% of the formulation. The oxidizing agent can be, for example, hydrogen peroxide. In one aspect, the sulindac gel formulation comprises 10% sulindac and 25% hydrogen peroxide.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
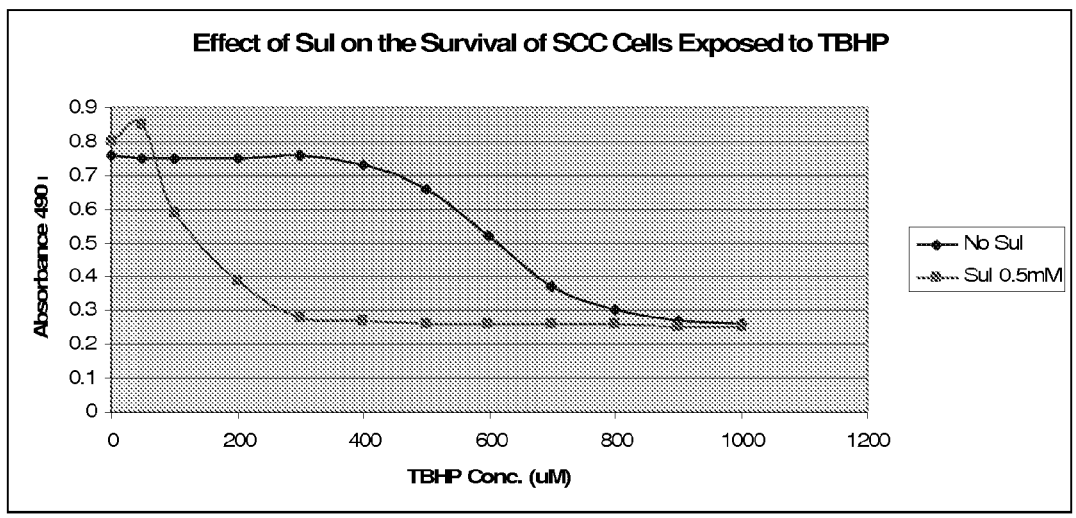
FIG. 1 is a graph showing the effect of TBHP on viability of SCC skin cancer cells following pretreatment with 500 µM sulindac. SCC skin cancer cells were incubated for 24 hr in the presence or absence of 500 µM sulindac. The medium was removed and the cells washed once with fresh medium followed by addition of medium containing the indicated concentration of TBHP. After a 2 hr incubation at 37° C., the cells were assayed for viability.

Treatment or prevention of a cancerous or precancerous disorder in humans or animals in need of such treatment or prevention is provided by methods and combinations using two or more components.

Definitions

In accordance with the present invention and as used herein, the following terms are defined with the following meanings, unless explicitly stated otherwise.

As used herein, "a", "an," and "the" include plural references unless the context clearly dictates otherwise.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma. The term "cancer" includes any cancer arising from a variety of chemical, physical, infectious organism cancer causing agents. For example, hepatitis B virus, hepatitis C virus, human papillomaviruses; sun; lead and lead compounds, X-rays, compounds found in grilled meats, and a host of substances used in textile dyes, paints and inks. Further details of cancer causing agents are listed in *The Report on Carcinogens*, Eleventh Edition. Federal law requires the Secretary of the Department of Health and Human Services to publish the report every two years.

Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

The term "sarcoma" generally refers to a tumor which is made up of a substance like the embryonic connective tissue and is generally composed of closely packed cells embedded in a fibrillar or homogeneous substance. Examples of sarcomas which can be treated with the compositions and optionally a potentiator and/or chemotherapeutic agent include, but not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions and optionally a potentiator and/or another chemotherapeutic agent include but not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions and optionally a potentiator and/or a chemotherapeutic agent include but not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Diagnostic" or "diagnosed" means identifying the presence or nature of a pathologic condition or a patient susceptible to a disease. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The treatment of neoplastic disease, cancer, or neoplastic cells, refers to an amount of the composition, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention of tumor cell infiltration into peripheral organs; (6) inhibition, including (i) reduction, (ii) slowing down or (iii) complete prevention of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

The terms "dosing" and "treatment" as used herein refer to any process, action, application, therapy or the like, wherein a subject, particularly a human being, is rendered medical aid with the object of improving the subject's condition, either directly or indirectly.

The term "therapeutic compound" as used herein refers to a compound useful in the prophylaxis or treatment of cancer.

The term "therapeutic combination" as used herein refers to the administered therapeutic compounds when administered in combination therapy, and to any pharmaceutically acceptable carriers used to provide dosage forms such that the beneficial effect of each therapeutic compound is realized by the subject at the desired time, whether the compounds are administered substantially simultaneously, or sequentially.

The compounds of the invention encompass various isomeric forms. Such isomers include, e.g., stereoisomers, e.g., chiral compounds, e.g., diastereomers and enantiomers.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space. Diastereoisomers that have the opposite configuration at only one of two or more tetrahedral stereogenic centres present in the respective molecular entities are known as "epimers." Thus, when used herein "sulindac" or variants, derivatives or oxides thereof, includes epimeric and enantiomeric molecules.

Furthermore the indication of configuration across a carbon-carbon double bond can be "Z" referring to what is often referred to as a "cis" (same side) conformation whereas "E" refers to what is often referred to as a "trans" (opposite side) conformation. Regardless, both configurations, cis/trans and/or Z/E are contemplated for the compounds for use in the present invention.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

Compositions

The present invention provides a composition comprising sulindac and hydrogen peroxide which effectively removes actinic keratoses, BCC, and SCC in several weeks without severe side effects. The pharmaceutical composition may be applied to specific sites or to relatively large areas of skin to treat visible actinic keratoses and skin cancers and to prevent the development of incipient actinic keratoses. The composition can be used simultaneously or in separate parts. The advantages of the present invention will be readily apparent from the discussion, description and examples which follow.

Briefly, we have shown that four tumor cell lines—two derived from skin (SCC and melanoma), and colon and lung cell lines—exhibit markedly increased sensitivities to killing by oxidative stress when pretreated with sulindac. Similar effects were observed with two different forms of direct oxidative stress—hydrogen peroxide and tert-butyl hydroperoxide (TBHP) or the use of arsenic trioxide, a compound that generates the production of ROS. This effect occurs at concentrations of each compound that individually have little or no activity directed against cancer cells. The killing effect was not observed when using normal human skin, colon, or lung cells. In contrast, the normal cells exhibited a protective effect with the combination of sulindac and peroxide at the lower concentrations of peroxide. Sulindac metabolites (sulindac sulfide in some instances and sulindac sulfone) also had enhanced killing effects of cancer cells when exposed to peroxide. Experiments with four other NSAIDS, (acetylsalicylic acid, ibuprofen, diclofenac sodium, and celecoxib) indicated that none were effective in producing the enhanced killing effects after exposure to the oxidating agents. The mechanism of action of this therapy may be associated with a selective increase in the ROS levels in cancer cells as opposed to normal cells which, in general, has an opposite effect leading to no change or a lowering in the levels of ROS. Thus, this drug combination can be useful for the selective treatment of cancer and precancerous conditions without the killing of normal cells.

The method comprises treatment with a therapeutically effective amount of a combination comprising two agents. The first agent is sulindac or its metabolites or derivatives. The second agent is an oxidizing agent or agent that leads to the generation of ROS. Besides being useful for human treatment, the present invention is also useful for veterinary treatment of companion animals, exotic animals and farm animals, including mammals, rodents, and the like. More preferred animals include horses, dogs, and cats.

The enhanced cancer cell killing effects of the combination of sulindac and an oxidizing agent has not been previously described. Without wishing to be bound by theory, sulindac functions as a catalytic anti-oxidant through the Msr system, thereby leading to an enhanced protection of cells (normal or cancerous) when given in combination with an oxidant.

The experimental results revealed that sulindac had a dual effect, in a sense a reverse effect, such that normal cells were protected but cancer cells were killed. This effect is specific to sulindac and is not seen with other NSAIDs. The mechanism of action suggests that cancer cells or highly proliferating cells, become more sensitive to the effects of ROS. Normal cells or cells that are not in a hyper-proliferative state are protected and become less sensitive to the effects of ROS. This dual effect of sulindac was totally unexpected and surprising. Details are provided in the examples which follow.

Polyps of the colon are precancerous growths that if left untreated can progress to adenocarcinoma of the colon in a significant number of patients. Once a polyp is detected in the colon, surgical intervention is recommended to remove or destroy the lesion. However, the need exists to develop chemoprevention strategies for patients that cannot tolerate polypectomy or who are unwilling or unable to have a protectomy. Sulindac has been known as an anti-inflammatory and analgesic drug since the early 1970's. It is claimed in U.S. Pat. No. 3,654,349 issued to Shen et al in 1972, and commercialized by Merck under the trade name CLINORIL. Several NSAIDs, originally developed to treat arthritis, such as sulindac have shown effectiveness in inhibiting and eliminating colonic polyps and in some cases, adenocarcinoma of the colon. Polyps virtually disappear when the NSAID that the patient takes is sulindac. However, the prophylactic use of currently available NSAIDs, even in polyposis syndrome patients, is marked by severe side reactions that include gastrointestinal irritations and ulcerations. Once sulindac treatment is terminated due to such complications, the polyps can return, particularly in polyposis syndrome patients.

The compounds used in the treatment of this invention are effective on precancerous and cancerous lesions either because they are active themselves or because they are metabolized to active derivatives. In a preferred embodiment, a structurally related compound can be substituted for both compounds e.g. Sulindac and peroxides).

Oxidizing groups contemplated for use in accordance with the present invention include peroxides, nitrates, nitrites, perchlorates, chlorates, chlorites, hypochlorite, dichromates, permanganates, and persulfates. Use of other electron accepting compounds including those not containing oxygen is within the scope of the invention as well. Bromine is an example of such a compound. Use of oxidizing agents or compounds that cause cells to produce ROS such as arsenic trioxide, retinoic acid (and its derivatives), K antimonyl tartrate, doxorubicin, imexon, and bortezomib are within the scope of this invention.

Examples of peroxide compounds for utilization in the present invention include, without limitation, hydrogen peroxide; organic peroxides; inorganic peroxides such as sodium peroxyborate tetrahydrate (sodium perborate tetrahydrate) and calcium peroxide; peroxide complexes such as urea hydrogen peroxide, and superoxide salts such as sodium superoxide. In aqueous solution, the superoxide free radical ($O_2^*$) dismutates (via reaction with its conjugate acid, the perhydroxyl free radical) to form hydrogen peroxide, and in biological systems the enzyme superoxide dismutase accelerates dismutation. Examples of organic peroxides include hydroperoxides (ROOH) such as lipid hydroperoxides, and internal peroxides such as artemisinin and its derivatives (an endoperoxide used in the treatment of malaria). Elf Atochem, Inc. (Philadelphia, Pa.) is a source of many organic peroxide compounds. Hydrogen peroxide of high purity can be obtained from Solvay Interox and other commercial sources. 1-Hydroperoxycyclohexyl-1-hydroxy cyclohexyl peroxide and tert-Butyl hydroperoxide can be obtained from Pfaltz and Bauer. Artemisinin can be obtained from Aldrich Chemical Company and Sigma Chemical Company. Sodium peroxyborate tetrahydrate can be obtained from Alfa Johnson Matthey and from Fluka Chemika Biochemika. Urea hydrogen peroxide is available from Aldrich Chemical Company. Methods for the preparation of fatty acid hydroperoxides (such as, for example, linolenic acid hydroperoxide, arachidonic acid hydroperoxide, and docosahexaenoic acid hydroperoxide) and of other lipid hydroperoxides (such as, for example, cholesterol hydroperoxide, cholesteryl linoleate hydroperoxide, trilinolein hydroperoxide, phosphatidylcholine hydroperoxide, and phosphatidylethanolamine hydroperoxide) are well known to those familiar with the art. Many other peroxide compounds are available from commercial sources, and include 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl)dioxy)-cyclohexanol. As used in this specification, and in the claims appended hereto, the term peroxide or peroxide compound is meant to be inclusive of hydrogen peroxide, inorganic peroxides, organic peroxides, peroxide complexes, other compounds containing the peroxy (peroxo) —O—O— moiety, superoxides, and peroxide precursor compounds which generate peroxide species in situ. Examples of organic peroxides include hydroperoxides, internal peroxides, endoperoxides, diacyl peroxides, ketone peroxides, peroxydicarbonates, peroxyesters, dialkyl peroxides, peroxyketals, and peroxyacids. Methods for the synthesis of organic peroxides are well known to those familiar with the art can be used in accordance with the present invention. Use of chromic acid, iodine, oxygen, ozone, peroxycarboxylic acids, permanganate, peroxyethanoic acid and peroxybenzoic acid is also contemplated. The primary effect of the oxidizing agent is to kill cellular material by binding a free radical molecule with the biological material and oxidizing the biological material. Therefore, it is also believed that any biologically active free radical, such as a heavy metal radical, may be effective.

Hydrogen peroxide has been used as a medicinal product for over a century. The germicidal power of hydrogen peroxide is well known and is due to the oxidizing effect of the peroxide. The main usage of hydrogen peroxide is in production of chemicals and bleaching of cellulose pulp and textiles. Small quantities are used for such purposes as disinfection of eye contact lenses, disinfections of wounds and mouth washing. Both hydrogen peroxide and carbamide peroxide are used for hair bleaching, oral antiseptics, dentifrices, oxidation of permanent waves, hair relaxers, ear drops, crank sores and tooth bleaching. Zinc peroxide is used as accelerator in rubber compounding, curing agent for synthetic elastomers and in cosmetic powders as antisepticals. Peroxide compounds including hydrogen peroxide and carbamide peroxide have been used in various dental procedures for many years. Reports of using peroxides to bleach or whiten teeth can be traced back to more than a century ago. Current peroxide containing whiteners used in USA can be classified into 3 categories: 1) Those containing high concentration of hydrogen peroxide (30-35%) or carbamide peroxide (35%) for professional use only; 2) materials that are dispensed by dentists and used by patients at home (up to 10% hydrogen peroxide or 16% carbamide peroxide); and 3) over-the-counter products with hydrogen peroxide content up to 6% and available to consumers for home use, such as Crest White Strips.

Hydrogen peroxide solutions of 35% or less would not be classified as skin irritants in rabbits by the European Union criteria (ECETOC, 1996). Skin irritation tests in rabbits with concentration of hydrogen peroxide of 3-8% were nonirritating to intact and abraded skin following exposure for 24 hours under occlusive dressing (ECETOC, 1996). Irritation was slight following 4 hour exposure to 10% hydrogen peroxide and mild with 35% hydrogen peroxide.

The concentration of the sulindac in the topical formulation can range from about 1% to 50% by weight. In one preferred embodiment, the sulindac is present in a concentration of about 5% or about 10% by weight. The carrier may further include humectants, fragrances, colors, thickeners, lubricants and preservatives, as is well known in the art. One particularly preferred humectant comprises a collagen derived material such as collagen laurate or the like. In some instances, the carrier may simply comprise water, whereas in other instances it may be a lotion based carrier and may typically include ingredients such as glycerine, propylene glycol, methyl and/or propyl paraben, hydroxyalkyl cellulose and the like. In one preferred embodiment, the carrier may comprise a hypo-allergenic, high lipid, cream based carrier.

Sulindac has been particularly well received among the NSAIDs for gastrointestinal polyp treatment. Sulindac is a sulfoxide compound that itself is believed to be inactive as an anti-arthritic agent. The sulfoxide is known to be converted by liver and other tissues to the corresponding sulfide, which is acknowledged to be the active moiety as a prostaglandin inhibitor. Recently, this conversion has been shown to be catalyzed by methionine sulfoxide reductase (MsrA). The sulfide, however, is associated with the side effects of conventional NSAIDs. Sulindac appears to be metabolized to sulindac sulfone by as yet unknown reactions. Sulindac sulfone is not an inhibitor of prostaglandin synthesis but has apoptotic activity against a wide array of cancer cells. The sulfone is currently being evaluated in Phase 2-3 clinical trials as therapy for multiple different types of cancers.

Hydrogen peroxide concentrations used in various methods according to the present invention can range from about 1% to 50% by weight and can be varied according to exposure time. A preferred range is about 1%-20%. It is believed that cell death can occur with exposures to concentrations of hydrogen peroxide as low as 3%. Preferably, the exposure time is less than 45 minutes, more preferably less than 15 minutes, and most preferably no more than 10 minutes. If the oxidizing agent is delivered on a strip or in a gel or other matrix, the exposure time may be very long and indefinite. One method utilizes a peroxide/adhesive mixture to provide a longer exposure.

When administered as a combination, the therapeutic agents can be formulated as separate compositions which are given at the same time or different times, or the therapeutic agents can be given as a single composition. The two components may be applied sequentially. In such a sequential application, the sulindac will have to be applied first followed by the peroxide. Preferably, the applications are made within one hour and most preferably, they are made within about one half hour of each other.

Accordingly, the present invention may be implemented in connection with a treatment kit. The kit includes a composition having the sulindac and the peroxide in a slow-release, two component delivery system such as within patches or strips at their effective concentrations, typically ranging from about 5% to 6%. The kit will also preferably include educational materials for optimum patient compliance and follow-up.

Separate kits may be provided for use by physicians and patients. The physician's kit will include relatively higher concentrations of the materials. It may be discovered that the effective concentrations for removing a precancerous growth are different than the concentrations needed to destroy a BCC or SCC.

In a preferred embodiment, the methods and pharmaceutical compositions of the present invention are used for the treatment or prevention of neoplasia disorders including the group consisting of acral lentiginous melanoma, actinic keratoses, adenocarcinoma, adenoid cystic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epithelioid, Ewing's sarcoma, fibrolamellar, focal nodular hyperplasia, gastrinoma, germ cell tumors, glioblastoma, glucagonoma, hemangioblastomas, hemangioendothelioma, hemangiomas, hepatic adenoma, hepatic adenomatosis, hepatocellular carcinoma, insulinoma, intraepithelial neoplasia, interepithelial squamous cell neoplasia, invasive squamous cell carcinoma, large cell carcinoma, leiomyosarcoma, lentigo maligna melanomas, leukoplakias, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

In another preferred embodiment, the pharmaceutical compositions of the invention selectively kill all cancers or hyper-proliferative pre-malignant cells. Included in these cell types are cancers arising from viruses or physical agents that would lead to hyper-proliferative states. For example, pox viruses create a hyper-proliferative state similar to a cancer. HPV causes papillomas and cervical polyps (fibroids) that are not malignant but are proliferations that may be affected by the combination.

In a preferred embodiment, a pharmaceutical composition comprises sulindac, sulindac metabolites, sulindac derivatives and an oxidating agent. Preferably, the sulindac metabolite comprises sulindac sulfide or sulindac sulfone.

In another preferred embodiment, the sulindac comprises R- and S-epimers of sulindac. Preferably, the sulindac is an R-epimer. We have discovered that the R-epimer of sulindac can retain its cancer killing effects. We have also found that in normal cells, but not cancer cells, the R-epimer of sulindac is not efficiently converted to the sulfide, the active COX inhibitor. Since COX inhibitors produce serious toxicity, it is expected that the R-epimer of sulindac can be a potentially superior therapeutic agent because it would have a lower toxicity profile in normal cells.

Figure 21:
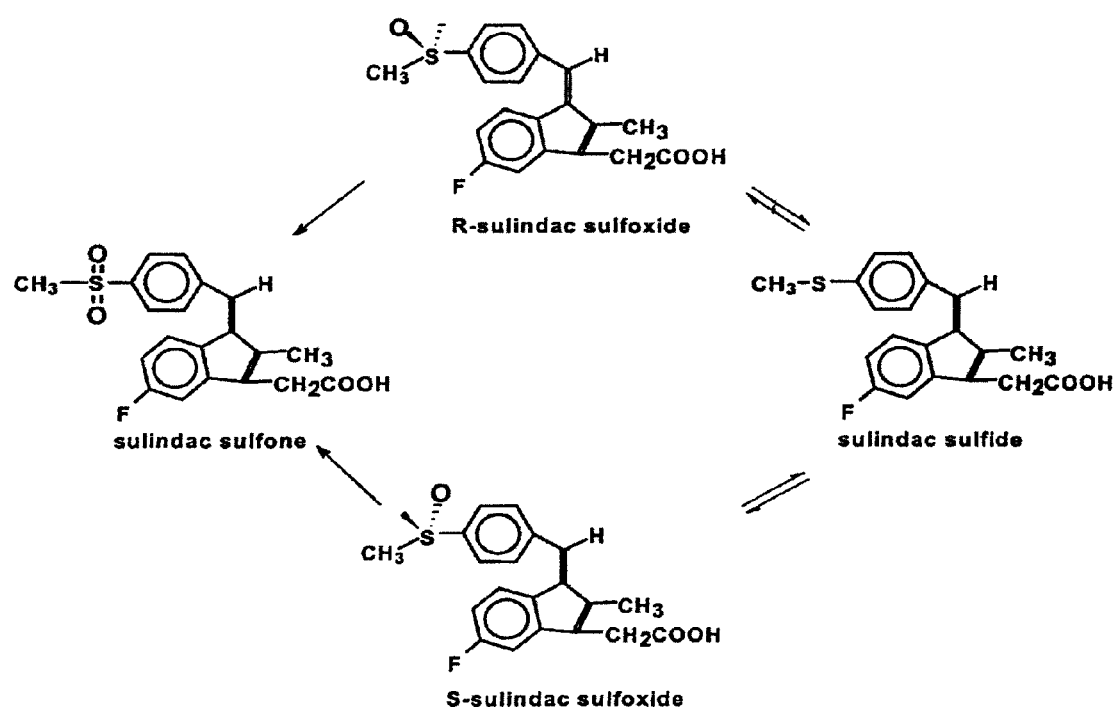
FIG. 21 is a schematic representation showing the structure of sulindac and its metabolites. Sulindac refers to a mixture of R- and S-epimers of sulindac sulfoxide. Theoretically, both the R-sulindac sulfoxide and S-sulindac sulfoxide can be oxidized to form sulindac sulfone or reduced to form sulindac sulfide.

Sulindac, unlike its metabolites, is a chiral compound since it contains a methyl sulfoxide moiety, in which there is asymmetry around the sulfur atom (FIG. 21). Therefore, the drug sulindac consists of an equal mixture of the R- and S-epimers, and would be a substrate for enzymes that are specific for either epimer. Reduction of either epimer of sulindac, which is a prodrug, will yield sulindac sulfide, which is the active COX inhibitor. The R-epimer of sulindac would be advantageous to other compounds as it would not be efficiently converted to a COX inhibitor in normal cells in vivo.

In another preferred embodiment, the oxidating agent comprises at least one of: peroxides, nitrates, nitrites, perchlorates, chlorates, chlorites, hypochlorite, dichromates, permanganates, and persulfates, bromine, arsenic trioxide, retinoic acid (and its derivatives), K antimonyl tartrate, doxorubicin, imexon, and bortezomib, hydrogen peroxide; inorganic peroxides, sodium peroxyborate tetrahydrate (sodium perborate tetrahydrate) calcium peroxide; peroxide complexes, urea hydrogen peroxide; superoxide salts, sodium superoxide; superoxide free radical ($O_2^*$) dismutates; organic peroxides, hydroperoxides (ROOH), lipid hydroperoxides, artemisinin and derivatives thereof; 1-Hydroperoxy-cyclohexyl-1-hydroxy cyclohexyl peroxide, tert-Butyl hydroperoxide; fatty acid hydroperoxides, linolenic acid hydroperoxide, arachidonic acid hydroperoxide, docosahexaenoic acid hydroperoxide, cholesterol hydroperoxide, cholesteryl linoleate hydroperoxide, trilinolein hydroperoxide, phosphatidylcholine hydroperoxide, phosphatidylethanolamine hydroperoxide; 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl) dioxy)-cyclohexanol; hydrogen peroxide, compounds containing a peroxy (peroxo) —O—O— moiety, superoxides, peroxide precursor compounds; endoperoxides, diacyl peroxides, ketone peroxides, peroxydicarbonates, peroxyesters, dialkyl peroxides, peroxyketals, and peroxyacids. Preferably, the oxidating agent is hydrogen peroxide, and/or tert-butyl hydroperoxide (TBHP), and/or arsenic trioxide.

In another preferred embodiment, the oxidizing agent is hydrogen peroxide in a concentration is in a range of about 1% to 50% by weight.

In another preferred embodiment, the sulindac concentration is in a range from about 1% to 50% by weight.

In yet another embodiment, the oxidizing agent is arsenic trioxide in a concentration in a range of about 1% to 50% by weight.

In another preferred embodiment, a topical pharmaceutical composition comprises a 5% sulindac gel and an oxidizing agent. Preferably, the 5% sulindac gel comprises: 71.08% deionized water; 12.00% SD Alcohol 40; 10% KOH; 5% Sulindac; 1% Hydroxy methyl cellulose; 0.50% Xantham gum; 0.20% GLYDANT PLUS (DMDMH&IPBC); 0.20% Citric Acid; and 0.02% disodium EDTA.

In other preferred embodiments, the sulindac gel is 10% sulindac, 15% sulindac, 20% sulindac, 50% sulindac.

In another preferred embodiment, a method of treating an abnormal cell, said method comprising administering to an abnormal cell a pharmaceutical composition comprising sulindac, or sulindac metabolites, or sulindac derivatives or combinations thereof, and an oxidating agent, thereby treating an abnormal cell. Preferably, the sulindac metabolite comprises sulindac sulfide or sulindac sulfone.

In another preferred embodiment, the oxidating agent comprises at least one of: peroxides, nitrates, nitrites, perchlorates, chlorates, chlorites, hypochlorite, dichromates, permanganates, and persulfates, bromine, arsenic trioxide, retinoic acid (and its derivatives), K antimonyl tartrate, doxorubicin, imexon, and bortezomib, hydrogen peroxide; inorganic peroxides, sodium peroxyborate tetrahydrate (sodium perborate tetrahydrate) calcium peroxide; peroxide complexes, urea hydrogen peroxide; superoxide salts, sodium superoxide; superoxide free radical ($O_2$*) dismutates; organic peroxides, hydroperoxides (ROOH), lipid hydroperoxides, artemisinin and derivatives thereof; 1-Hydroperoxycyclohexyl-1-hydroxy cyclohexyl peroxide, tert-Butyl hydroperoxide; fatty acid hydroperoxides, linolenic acid hydroperoxide, arachidonic acid hydroperoxide, docosahexaenoic acid hydroperoxide, cholesterol hydroperoxide, cholesteryl linoleate hydroperoxide, trilinolein hydroperoxide, phosphatidylcholine hydroperoxide, phosphatidylethanolamine hydroperoxide; 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl)dioxy)-cyclohexanol; hydrogen peroxide, compounds containing a peroxy (peroxo) —O—O— moiety, superoxides, peroxide precursor compounds; endoperoxides, diacyl peroxides, ketone peroxides, peroxydicarbonates, peroxyesters, dialkyl peroxides, peroxyketals, and peroxyacids. Preferably, the oxidating agent is hydrogen peroxide and/or tert-butyl hydroperoxide (TBHP), and/or arsenic trioxide.

In another preferred embodiment, the oxidizing agent, hydrogen peroxide, concentration is in a range of about 1% to 50% by weight.

In another preferred embodiment, the sulindac concentration is in range from about 1% to 50% by weight.

In another preferred embodiment, the oxidizing agent, arsenic trioxide, concentration is in a range of about 1% to 50% by weight.

In another preferred embodiment, the pharmaceutical composition comprises a 5% sulindac gel and an oxidizing agent. Preferably, the 5% sulindac gel comprises: 71.08% deionized water; 12.00% SD Alcohol 40; 10% KOH; 5% Sulindac; 1% Hydroxy methyl cellulose; 0.50% Xantham gum; 0.20% GLYDANT PLUS (DMDMH&IPBC); 0.20% Citric Acid; and 0.02% disodium EDTA.

In other preferred embodiments, the sulindac gel is 10% sulindac, 15% sulindac, 20% sulindac, 50% sulindac.

In yet another embodiment, a method of treating cancer, said method comprising administering to a cancer cell a pharmaceutical composition comprising sulindac, or sulindac metabolites, or sulindac derivatives or combinations thereof, and an oxidating agent, thereby treating cancer. Sulindac, sulindac metabolites, sulindac derivatives and an oxidating agent. Preferably, the sulindac metabolite comprises sulindac sulfide or sulindac sulfone.

In another preferred embodiment, the oxidating agent comprises at least one of: peroxides, nitrates, nitrites, perchlorates, chlorates, chlorites, hypochlorite, dichromates, permanganates, and persulfates, bromine, arsenic trioxide, retinoic acid (and its derivatives), K antimonyl tartrate, doxorubicin, imexon, and bortezomib, hydrogen peroxide; inorganic peroxides, sodium peroxyborate tetrahydrate (sodium perborate tetrahydrate) calcium peroxide; peroxide complexes, urea hydrogen peroxide; superoxide salts, sodium superoxide; superoxide free radical ($O_2$*) dismutates; organic peroxides, hydroperoxides (ROOH), lipid hydroperoxides, artemisinin and derivatives thereof; 1-Hydroperoxycyclohexyl-1-hydroxy cyclohexyl peroxide, tert-Butyl hydroperoxide; fatty acid hydroperoxides, linolenic acid hydroperoxide, arachidonic acid hydroperoxide, docosahexaenoic acid hydroperoxide, cholesterol hydroperoxide, cholesteryl linoleate hydroperoxide, trilinolein hydroperoxide, phosphatidylcholine hydroperoxide, phosphatidylethanolamine hydroperoxide; 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)-diisopropylbenzene, and 1-((hydroperoxycyclohexyl)dioxy)-cyclohexanol; hydrogen peroxide, compounds containing a peroxy (peroxo) —O—O— moiety, superoxides, peroxide precursor compounds; endoperoxides, diacyl peroxides, ketone peroxides, peroxydicarbonates, peroxyesters, dialkyl peroxides, peroxyketals, and peroxyacids. Preferably, the oxidating agent is hydrogen peroxide, and/or tert-butyl hydroperoxide (TBHP), and/or arsenic trioxide.

In another preferred embodiment, the oxidizing agent is hydrogen peroxide in a concentration is in a range of about 1% to 50% by weight.

In another preferred embodiment, the sulindac concentration is in range from about 1% to 50% by weight.

In yet another embodiment, the oxidizing agent is arsenic trioxide in a concentration in a range of about 1% to 50% by weight.

In another preferred embodiment, a topical pharmaceutical composition comprises a 5% sulindac gel and an oxidizing agent. Preferably, the 5% sulindac gel comprises: 71.08% deionized water; 12.00% SD Alcohol 40; 10% KOH; 5% Sulindac; 1% Hydroxy methyl cellulose; 0.50% Xantham gum; 0.20% GLYDANT PLUS (DMDMH&IPBC); 0.20% Citric Acid; and 0.02% disodium EDTA.

In other preferred embodiments, the sulindac gel is 10% sulindac, 15% sulindac, 20% sulindac, 50% sulindac.

Cancer Therapy:

In accordance with the invention tumor target cells are selectively targeted by the compositions. Tumors can be the result of infection by a tumor causing virus or other means.

In another preferred embodiment, abnormal or cancer cells are targeted by the compositions. For example, many malignancies are associated with the presence of foreign DNA, e.g. Bcr-Abl, Bcl-2, HPV.

The invention in general provides a method for treating diseases, such as cancer and diseases which are caused by infectious agents such as viruses, bacteria, intra- and extracellular parasites, insertion elements, fungal infections, etc., which may also cause expression of gene products by a normally unexpressed gene, abnormal expression of a normally expressed gene or expression of an abnormal gene.

The methods of the invention are preferably employed for treatment or prophylaxis against diseases caused abnormal cell growth and by infectious agents, particularly for treatment of infections as may occur in tissue such as lung, heart, liver, prostate, brain, testes, stomach, intestine, bowel, spinal cord, sinuses, urinary tract or ovaries of a subject.

In another preferred embodiment, the compositions of the invention can be administered in conjunction with chemotherapy. These chemotherapeutic agents can be co-administered, precede, or administered after the compositions. Non-limiting examples of chemotherapeutic agents include, but not limited to: cyclophosphamide (CTX, 25 mg/kg/day, p.o.), taxanes (paclitaxel or docetaxel), busulfan, cisplatin, cyclophosphamide, methotrexate, daunorubicin, doxorubicin, melphalan, cladribine, vincristine, vinblastine, and chlorambucil.

In another preferred embodiment, the pharmaceutical composition, inhibits the tumor cell growth in a subject, and the method comprises administering to the subject a pharmaceutical composition comprising a therapeutically effective amount of the composition. Inhibition of tumor cell growth refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

Combination Therapies:

The therapeutic compositions of the present invention may be combined with any other methods generally employed in the treatment of the particular tumor, disease or disorder that the patient exhibits. So long as a particular therapeutic approach is not known to be detrimental to the patient's condition in itself, and does not significantly counteract the instant composition treatment, its combination with the present invention is contemplated.

Therapeutic agents can include, for example, chemotherapeutic agents such as, cyclophosphamide (CTX, 25 mg/kg/day, p.o.), taxanes (paclitaxel or docetaxel), busulfan, cisplatin, methotrexate, daunorubicin, doxorubicin, melphalan, cladribine, vincristine, vinblastine, chlorambucil, tamoxifen, taxol, etoposide (VP-16), adriamycin, 5-fluorouracil (5FU), camptothecin, actinomycin-D, mitomycin C, cisplatin (CDDP), combretastatin(s) and derivatives and prodrugs thereof.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

The skilled artisan is directed to "Remington's Pharmaceutical Sciences" 15th Edition, chapter 33, in particular pages 624-652, for non-limiting examples of other chemotherapeutic agents that can be used in combination therapies with the PWM-poly IC-PHA compositions. Some variation in dosage will necessarily occur depending on the condition of the subject being treated. The physician responsible for administration will be able to determine the appropriate dose for the individual subject.

In connection solid tumor treatment, the present invention may be used in combination with classical approaches, such as surgery, radiotherapy, chemotherapy, and the like. The invention therefore provides combined therapies in which the therapeutic compositions are used simultaneously with, before, or after surgery or radiation treatment; or are administered to patients with, before, or after conventional chemotherapeutic, radiotherapeutic or other anti-angiogenic agents, or targeted immunotoxins or coaguligands.

When one or more agents are used in combination with the sulindac-peroxide compositions there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

To practice combined anti-tumor therapy, one would simply administer to an animal the composition in combination with another anti-cancer agent in a manner effective to result in their combined anti-tumor actions within the animal. The agents would therefore be provided in amounts effective and for periods of time effective to result in their combined presence within the tumor vasculature and their combined actions in the tumor environment. To achieve this goal, the compositions and other anti-cancer agents may be administered to the animal simultaneously, either in a single composition, or as two distinct compositions using different administration routes.

Alternatively, the composition mediated treatment may precede, or follow, the a second anti-cancer agent treatment by, e.g., intervals ranging from minutes to weeks. In certain embodiments where the anti-cancer agent and the composition are applied separately to the animal, one would ensure that a significant period of time did not expire between the time of each delivery, such that the anti-cancer agent and the composition would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The general use of combinations of substances in cancer treatment is well known. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the sulindac-oxide composition treatment, and another treatment was intended to prevent micrometastasis or tumor re-growth, such as the administration of an anti-angiogenic agent.

It also is envisioned that more than one administration of either the composition or another anti-cancer agent will be utilized. The composition and anti-cancer agents may be administered interchangeably, on alternate days or weeks; or a sequence of the composition treatment may be given, followed by a sequence of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

Cytokine therapy also has proven to be an effective partner for combined therapeutic regimens. Various cytokines may be employed in such combined approaches. Examples of cytokines include IL-1α, IL-β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

Effective Amounts

The compositions described above are preferably administered to a subject in an effective amount. An effective amount is an amount which is capable of producing a desirable result in a treated animal or cell (for example, to induce apoptosis or impair mitosis in a cell in the animal or a culture). As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for topical administration of the sulindac in the topical formulation can range from 1% to 25%. In the preferred embodiment, the sulindac is present in a concentration of 5% or 10%. An effective amount for use with a cell in culture will also vary, but can be readily determined empirically (for example, by adding varying concentrations to the cell and selecting the concentration that best produces the desired result). It is expected that an appropriate concentration would be in the range of about 1-5000 μM.

Method for Inhibiting Cancer Cell Growth

The invention provides a method for inhibiting tumor cell growth or increasing the rate of tumor cell apoptosis. The method includes the steps of contacting a tumor cell with a composition including a sufficient amount of sulindac-oxide compositions to kill or at least retard mitosis in the tumor cell. The method may be used to inhibit the growth of numerous types of cancerous tumor cells. The compositions have been tested and shown to be effective against different types of tumors such as melanoma, squamous, and breast cancer cells. (See, examples which follow). Sulindac (or related compounds thereof) comprising compositions are expected to be effective against other cancers as well, particularly those derived from epithelial, mesenchymal, and hemopoietic origins.

Any suitable formulation of sulindac-peroxide can be used in methods of the invention. Typical formulations are topical liposomal formulations of the compositions of varying concentrations. In addition to topical administration, sulindac-peroxide containing formulations can be administered to a subject via injection (e.g., IP, IV, IM, SQ).

In preferred embodiments, administration of sulindac-oxide compositions results in one or more phenotypes of a tumor cell being inhibited. For example, inhibition of tumor growth, reduction of tumor size, inhibition of metastasis, reduction in the number of tumor cells and the like. Each of these phenotypes of a tumor cell can be measured using standard assays, such as for example, imaging, mechanical measurements, in vitro assays and the like.

Formulations

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, inhalation or infusion techniques.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

The methods and combinations of the present invention provide one or more benefits. Combinations of the present invention may allow for a lower dose of each agent. A benefit of lowering the dose of the compounds, compositions, agents and therapies of the present invention administered to a mammal includes a decrease in the incidence of adverse effects associated with higher dosages.

By lowering the incidence of adverse effects, an improvement in the quality of life of a patient undergoing treatment for cancer is contemplated. Further benefits of lowering the incidence of adverse effects include an improvement in patient compliance, a reduction in the number of clinical visits needed for the treatment of adverse effects, and a reduction in the administration of analgesic agents needed to treat pain associated with the adverse effects.

Alternatively, the methods and combination of the present invention can also maximize the therapeutic effect at higher doses.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

The composition of the invention can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment of cancer with topical formulations of the composition, in other aspects of the invention the composition can be delivered by other methods. For example, the composition can be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. Compositions of the invention can also be administered in vitro to a cell (for example, to induce apoptosis in a cancer cell in an in vitro culture) by simply adding the composition to the fluid in which the cell is contained.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, i.e. sulindac, peroxide, arsenic trioxide is facilitated. Without violating this constraint, the pH may be selected to improve the compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of the composition. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

Kits and Formulations

The invention also provides a kit for reducing the rate of tumor growth in a subject. The kit of the invention includes a composition comprising sulindac, sulindac derivatives, variants etc, oxides such as hydrogen peroxide, arsenic trioxide etc, and, optionally a pharmaceutically acceptable carrier as well as printed instructions for using the composition to reduce the rate of tumor growth in a subject.

Active components can be present in solid, semi-solid or liquid form. Solid forms include for example, powders, granules and flakes. Semi-solid forms include, for example, gels, creams, gelatins and ointments. These and other active agents embraced by the present invention are known to those of ordinary skill in the art and, in most cases, are commercially available from suppliers such as Compound Solutions, Inc., Escondido, Calif. Information on these and other active and inactive agents embraced by the invention, and their commercial suppliers is available from various trade manuals, most particularly, Remington's Pharmaceutical Sciences, United States Pharmacopoeia (USP), National Formulary (NF), Merck Index, Physician's Desk Reference (PDR) and Chemical Abstracts.

The kits of the invention will also generally contain at least one inactive agent. As used herein, inactive agents are agents which do not provide any therapeutic benefit to the subject to whom they are administered. Instead, inactive agents can function in many other ways such as to provide a base in which the active agent can be dissolved or suspended, to dilute the active agent in order to provide proper doses upon administration, to facilitate the dissolution or suspension of the active agent, or to prevent oxidation of the active agent by removing air bubbles from the final compounded suspension. In some embodiments of the invention, the kits lack an inactive agent, and rather contain two or more active agents.

Base agents such as creams, oils, gels or ointments are suitable for topical or suppository applications. The choice of suitable inactive base agent for use in the kits of the invention will depend upon the active agent to be compounded. Suitable base agents will be known to the ordinary artisan. Alternatively, Remington's Pharmaceutical Sciences, the Physician Desk Reference (PDR) or other manuals as listed above, can be consulted in making this determination.

Examples of inactive base agents or components include, for example, lanolin, hydrophilic ointment, white ointment, yellow ointment, polyethylene glycol ointment, petrolatum, hydrophilic petrolatum, white petrolatum, rose water ointment, squalene, hydrogenated vegetable oil (Type II), ultrasound gel, pluronic lecithin organogel (PLO) gel, cream.

The term "petrolatum" as used herein means petrolatum ointment, petrolatum gel or petrolatum cream, all of which are commercially available. It is well within the realm of the ordinary pharmaceutical artisan to determine which form of petrolatum is most appropriate for a specific kit.

A commercially available ultrasound base is either POLYSONIC™ (ultrasound gel) ultrasound lotion or Aquasonic ultrasound 100 gel manufactured by Parker Laboratories, Inc. (Fairfield, N.J.) or ECOGEL (Coupling/Ultrasound Gel or Lotion) 100 or ECOGEL (Coupling/Ultrasound Gel or Lotion) 200 manufactured by Eco-Med (Mississauga, Ontario, Canada), the compositions of which may include cetyl alcohol, liquid paraffin, polymer, surfactants, preservatives such as propyl paraben and methyl paraben in bacteriostatic concentration, fragrance, and reverse osmosis water. As used herein, a gel is a base with a higher viscosity than a lotion. The physical characteristics of the POLYSONIC™ (ultrasound gel) ultrasound lotion and the ECOGEL (Coupling/Ultrasound Gel or Lotion) 100 include pH range of 6.5-7.0, density of 1.04 g/cm3, viscosity of 35,000 to 70,000 cps and acoustic impedence of 1.60 (105 g/cm2 sec). The physical characteristics of AQUASONIC ultrasound 100 gel or ECOGEL (Coupling/Ultrasound Gel or Lotion) 200 are similar to those of POLYSONIC™ (ultrasound gel) ultrasound lotion and ECOGEL (Coupling/Ultrasound Gel or Lotion) 100 except that their viscosity is 80,000 to 110,000 cps. These lotions and gels are available in a clear, colorless form or in a blue colored form.

Liquid bases are recommended for orally administered pharmaceuticals. In some embodiments of the invention, at least one active agent, will be supplied already co-mingled with an inactive agent. Examples of this include the combination of magnesium hydroxide and aluminum hydroxide (commercially available as MAALOX™ (magnesium hydroxide/aluminum hydroxide)), and diphenhydramine HCl (commercially available as BENADRYL™ (diphenhydramine hydrochloride)). Both MAALOX™ (magnesium hydroxide/aluminum hydroxide) and BENADRYL™ (diphenhydramine hydrochloride) are supplied by their respective manufacturers as a combination of active and inactive agents.

Sterile base solutions are preferred for parenteral (i.e., injection), aerosol (i.e., inhalation) and ophthalmic routes of administration. The administration may, for example, be intravenous, intraperitoneal, intramuscular, intracavity, subcutaneous or transdermal. Preparations for parenteral administration includes sterile aqueous or nonaqueous solutions, suspensions and emulsions. The compounded pharmaceuticals, preferably those intended for parenteral, inhalation or ophthalmic routes of administration, may be prepared and administered in inactive agents which are pharmaceutically-acceptable. As used herein, a pharmaceutically-acceptable carrier means a non-toxic material that does not interfere with the effectiveness of the biological activity of the active agents and that is compatible with the biological systems such of a tissue or organism. The physiologically acceptable carrier must be sterile for in vivo administration. Pharmaceutically acceptable carriers include diluents, fillers, salts, buffers, stabilizers, solubilizers and other materials which are well-known in the art. The characteristics of the carrier will depend on the route of administration. In general, pharmaceutically-acceptable agents or carriers are well-known to those of ordinary skill in the art. In some embodiments, suitable sterile solutions include albuterol and ipratropium inhalation solution; papaverine, phentolamine and prostaglandin injection solution; fentanyl citrate injection solution and cyclosporine ophthalmic drops.

Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

Inactive agents may also include components which function to preserve the integrity of the compounded formulation. This latter category of inactive agents includes, for example, anti-foaming agents. Anti-foaming agents are agents which function to remove unwanted air trapped in a composition, perhaps during mixing or agitation. The use of anti-foaming components is particularly useful in the preparation of pharmaceuticals to be used for ultrasound imaging due to the impedance of signal transmission by air bubbles. Examples of other anti-foaming agents useful in the compositions of the invention include bisphenylhexamethicone, dimethicone, dimethiconol, hexamethyldisiloxane, hexyl alcohol, isopropyl alcohol, petroleum distillates, phenethyl disiloxane, phenyl trimethicone, polysilicone-7, propyl alcohol, silica dimethyl silylate, silica silylate, tetramethyl decynediol and trimethylsiloxysilicate. A preferred anti-foaming agent is simethicone. Simethicone is a mixture of about 90% dimethicone and 10% silicone dioxide (w/w). Simethicone is used extensively as an anti-gas agent in pharmaceutical products such as GAS-X™ (simethicone), MAALOX™ (magnesium hydroxide/aluminum hydroxide), MYLANTA™ (aluminum, magnesium simethicone), PHAZYME™ (simethicone), GENAZYME™ (simethicone), and MYLICON™ (simethicone) Drops. Simethicone may be used as an anti-foaming agent in any of the formulations embraced by the invention.

Other inactive agents which can be included in the formulations of the invention include stabilizers such as citric acid, anti-oxidants such as sodium metabisulfite and preservatives such as methyl or propyl paraben.

Another class of inactive agents is suspending agents. Suspending agents are agents which facilitate the suspension and in some cases the dissolution of an active agent in a base. Generally, suspending agents ensure more uniform mixing of active and base components. In order to administer a more uniform dose of a compounded pharmaceutical to a patient, the compounded components must be properly and homogeneously combined. If the active agent is present as a powder, a uniform dispersion is sometimes difficult to achieve using the traditional form of compounding.

A subcategory of suspending agents are solubilizers. Solubilizers are agents which facilitate the dissolution of a solid or, in some cases, a semi-solid agent in a base inactive agent. In some embodiments of the invention, a solid-form active agent may be dissolved in a suspending agent, prior to mixing it with the base agent. Conversely, the suspending agent and the base agent may be prepackaged together, particularly if the concern is ensuring the uniform blending of active agent within the base component rather than the loss of solid (i.e., powdery) active agent. In still other variations, the suspending agent may be premixed with the base inactive agent.

Suitable suspending agents useful in the compositions of the invention include, but are not limited to, glycerin, hexylene glycol, propylene glycol, sorbitol, acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, benzalkonium chloride, benzethonium chloride, cetylpyridinium chloride, docusate sodium, nonoxynol 9, nonoxynol 10, octoxynol 9, polyoxyl 50 stearate, and tyloxapol.

Still other suspending agents include humectants and wetting agents. Humectants are agents which retain moisture. Examples of humectants include but are not limited to glycerin, hexylene glycol, propylene glycol and sorbitol. The amounts of base and non-base inactive agents will also depend upon the particular compounded pharmaceutical to be made. Base agents can be provided in quantities corresponding to final compounded preparations which contain 0.5% to 99.99% of base agent, either in weight or in volume. In preferred embodiments, the final concentration of the base agent is 20%-80%. In even more preferred embodiments, the final concentration of the base agent is 40%-80%.

Generally, the amounts of non-base agents will be sufficient to provide final formulations in which each non-base inactive agent represents 0.01%-50% (w/w) of the composition. Suspending agents may represent 1%-50% (w/w) of the final formulation. Preferably, suspending agents will represent 1%-40% and even more preferably, they will represent 5%-30% of the final formulation. Anti-foaming agents may represent 0.01% to 20% (w/w) of the final formulation. More preferably, anti-foaming agents represent 0.05% to 10% of the final formulation and even more preferably, they represent 0.1% to 5% of the final formulation.

In some preferred embodiments, the single or multiple unit of use kits are designed to yield, after the physical mixing of active and inactive agents, compounded pharmaceutical formulations comprising 0.1%, 5%, 10% to 99% w/w of sulindac or variants thereof.

The kits of the invention will provide each and every component required for preparing a given compounded pharmaceutical in pre-measured quantities. The measuring of each component will be performed using current Good Manufacturing Practices (cGMP, as legislated by the Code of Federal Regulations or CFR), as will the packaging and labeling of each component and the final packaging and labeling of the kit in its entirety. In this way, the kits are standardized and variations from batch to batch will be minimal or non-existent and the precision and accuracy in the measurement of individual components will be improved considerably over the methods currently used by pharmacists. Instructions may be provided as separate from any container, but still contained in the kit. Alternatively, instructions may be located on a container, for example, on an exterior surface or on an interior surface such as a lid.

Both the active and the inactive agents of the kit are provided in containers. Since the kit will contain at least one active and at least one inactive agent, or at least two active agents pre-formulated with inactive agents, the minimum number of containers in a given kit will be two. In preferred embodiments, the maximum number of containers in a kit will be less than or equal to four. The containers may be formed in any size or shape useful for the mixing or transferring of components from one container to another. For example, each container may be in the form of vials, bottles, squeeze bottles, jars, sealed sleeves, envelopes or pouches, tubes or blister packages or any other suitable form provided the container is sealed so as to prevent premature mixing of components. As used herein, a container may also be a compartment or a chamber within a vial, a tube, ajar, or an envelope, or a sleeve, or a blister package or a bottle, provided that the contents of one compartment are not able to associate physically with the contents of another compartment prior to their deliberate mixing by a pharmacist or physician.

The invention intends to provide within a single kit all the necessary components, containers and stirring or mixing elements for preparing a unit of use compounded pharmaceutical without the need for other accessories. The kits of the invention may also contain items such as gloves or spill pads. Individuals skilled in the art can readily modify the choice of container to suit the individual components housed and mixed therein.

In some embodiments of the invention, the final compounded formulation will be provided to the patient in the container originally housing the inactive, or base, compound. In other embodiments, the final compounded formulation will be provided in the container originally housing the active agent. In still other embodiments, all the necessary components for preparing a compounded pharmaceutical are included in one container but are physically separated within such a container. For example, an inactive agent may be contained in the lower part of a container, such as a jar, and may be covered by a plastic, peel-off wrap. The active agent may be housed in this same jar, but secured to the lid of the jar and provided in a pouch or a sleeve. The ability to provide all components together in the smallest packaging arrangement may be preferable in some circumstances. Mixing elements required in the preparation of the compounded pharmaceutical may also be located within the same container, for example, secured to the inside surface of the lid of the container.

In still another embodiment of the invention, active and inactive agents are provided in adjacent compartments of a single housing container, and are mechanically removed from these compartments and into a third compartment. As an example, all the chemical components necessary to prepare a particular compounded pharmaceutical can be present in a single tube, for example, a tube similar to a toothpaste tube having an interior which is divided into separate compartments. Each of these compartments in turn house a base agent or an active agent. Either the base agent or the active agent may be premixed with an anti-foaming agent and/or a suspending agent, as described herein. By applying pressure on the tube as a whole, the components are made to exit their respective compartments. They can then be mixed either in an adjacent or a physically separate compartment. Squeezing or pressing of the outside surface of the tube may be all that is necessary to retrieve the individual components housed within the tube. In yet another embodiment, the contents of both chambers of a container can be pumped out and into a third container. In a related embodiment, it is also envisioned that rather than requiring the contents of each compartment to exit and flow into a third compartment, the components may be separated by a removable sheet or film. Thus, upon removal of such a sheet or film, the contents of the two compartments are in contact and may require only agitation or end-over-end inversion to become completely mixed. This latter embodiment would eliminate the need for a mixing element, and potentially for an exterior package particularly if the instructions are written on the container itself.

According to some aspects of the invention, each container may contain one or more active agents or one or more inactive agents. For example, in some embodiments of the invention, none of the containers may contain both an active and an inactive agent prior to mixing by the pharmacist or physician. However, the invention also provides for kits in which a container may contain an active and at least one inactive agent, such as a base agent, a suspending agent or an anti-foaming agent.

In a preferred embodiment, the active agent is provided premixed with an inactive agent. This applies mainly when sulindac will be commercially available as a solid, for example a powder, and the pre-mixing of the powder with a suspending agent facilitates the compounding by the pharmacist or physician. In yet other embodiments, at least two of the inactive agents may be pre-mixed as provided in the kits of the invention.

In some embodiments, where the active agent is added to the base component, it may be desirable to provide the base component in a container which is only partially full. In preferred embodiments, the container in which the base component is situated is less than 100% full by volume. In other embodiments, the containers are 95%, 90%, 80%, 75%, 70%, 60%, 50%, 40%, 30%, 25%, 20% or less than 20% full by volume. In other embodiments, the active or inactive agents comprise a volume of their respective containers ranging from 100% to greater than 1%, and every integer there between. In preferred embodiments, the inactive agent occupies a volume of the second container which is less than or equal to the volume of the second container minus the volume of the active agent.

As used according to the invention, the active and inactive agents are physically combined by a pharmacist to produce a compounded pharmaceutical. The components of the kit can be combined by gentle agitation, shaking, stirring, folding or end-over-end inversion of the first or second container. In some instances, the proper mixing of the active and inactive agents may be accomplished simply by adding one to the other, followed by sealing and agitation of the container. This is especially the case if the components are both liquids or both semi-solids. In other instances, it may be necessary to stir the components together with a mixing element. Mixing elements are well known to a person of ordinary skill in the pharmaceutical arts and may include for example, centrifuges, a mixing rod such as a glass rod, a spoon, a spatula or a dipstick. Where required, the mixing element is provided in the kit. The presence of a mixing element will vary depending on the compounded pharmaceutical formulation to be made with the components of a kit.

The final compounded pharmaceutical may be formulated into preparations in solid, semi-solid, liquid or gaseous forms such as tablets, capsules, powders, granules, ointments, solutions, suppositories, inhalants and injections, and usual ways for oral, parenteral or surgical administration. The invention also embraces locally administering the compounded pharmaceuticals of the invention such as, for example, as implants. These formulations may be intended for oral, topical, mucosal, parenteral (e.g., injectable), rectal or vaginal administration. In preferred embodiments, the final compounded formulations may be self-administered.

The kits of the invention may also contain a package which may be compartmentalized to receive in close confinement two or more containers of the invention. In some embodiments, the package may be box-like, being made of a moderately rigid material such as cardboard or reinforced paper. In other embodiments, the package may be a bag. In still other embodiments, as described herein, there is no external packaging and all containers may be incorporated into one of the containers housing either an active or an inactive agent. This latter embodiment can be accomplished by securing containers such as pouches, sleeves or sacs, containing either active or inactive agents, as well as any mixing elements required for the compounding, to the interior of the lid of the main container. An individual skilled in the art can readily modify the package to suit the individual needs of each kit and each use. The kits of the invention further contain instructions for the proper use of the components found therein.

The kits of the invention are intended for use in the treatment or prevention of a number of disorders in a variety of subjects including humans, dogs, cats, horses, fish, pigs, cows, sheep, deer, zoo animals and laboratory animals (e.g., mice, rats, rabbits, monkeys, etc.). The invention intends to embrace unit of use kits containing the above preparations.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

Killing of Skin Cancer Cells

Sulindac enhances the killing of the human SCC-25 squamous cell skin cancer cell line by tert-butyl hydroperoxide (TBHP). SCC-25 is a human squamous cell carcinoma cell line developed by J G Rheinwald [Rheinwald, 1981]. The cells are obtained from the American Type Culture Collection (ATCC # CRL-1628). The cells were maintained in minimum essential medium (Eagle) supplemented with 2 mM L-glutamine, Earle's BSS containing 1.5 g/L sodium bicarbonate, 0.1 mM non-essential amino acids, 1.0 mM sodium pyruvate and 10% fetal bovine serum.

The experimental approach was to pretreat SCC cells with sulindac for 24 hr prior to exposure to TBHP for 2 hr. Sulindac (Sigma; S-8139) was freshly prepared as a 1M stock solution in 1M Tris.Cl, pH 8.0. SCC cells were suspended in culture medium containing 10% fetal bovine serum at a cell density of $6 \times 10^5$ cells/ml. Cell suspensions containing 500 µM sulindac or no sulindac (Control) were plated in 96 well microtiter plates with a total of $6 \times 10^4$ cells per well. The plates were incubated for 24 hr at 37° C. in a 5% $CO_2$ incubator. The culture medium was then removed and the cells washed once with fresh culture medium without serum. After removal of the wash solution, fresh culture medium without serum that contained the indicated final concentration of TBHP was added to the cells for 2 hrs. Serum was omitted from the medium during the two-hour exposure to TBHP since TBHP may be rapidly depleted in the presence of serum.

Cell viability was determined by the CELLTITER 96®-Aqueous One Cell Proliferation Assay (Promega) according to the manufacturer's instructions. The assay utilizes a novel tetrazolium compound (3-(4,5-dimethylthiazol-2-yl)-5-(3-carboxymethoxyphenyl)-2-(4-sulfophenyl)-2H-tetrazolium; MTS) and an electron-coupling reagent (phenazine ethosulfate; PES). Metabolically active cells convert the MTS to a water-soluble formazan by the action of cellular dehydrogenases. The amount of formazan produced is measured by absorbance at 490 nm using a colorimetric microtiter plate reader (BIORAD; Model 2550). Absorbance is directly proportional to the number of viable cells.

Experiments to determine the toxicity of sulindac showed no detectable effect on cell viability using the MTS assay at concentrations below 1 mM. Therefore, a concentration of 500 µM sulindac was used for the majority of our experiments in cancer cell lines.

Experiments were performed with the SCC skin cancer cells that were pretreated with 500 µM sulindac using TBHP. The combination of pretreatment with sulindac and oxidative stress by addition of TBHP enhanced the killing of the SCC carcinoma cells (FIG. 1). The decrease in viability of SCC cells pretreated with 500 µM sulindac was evident at concentrations of TBHP from 100 µM to 700 µM.

FIG. 1 shows the effect of TBHP on viability of SCC skin cancer cells following pretreatment with 500 µM sulindac. SCC skin cancer cells were incubated for 24 hr in the presence or absence of 500 µM sulindac. The medium was removed and the cells washed once with fresh medium followed by addition of medium containing the indicated concentration of TBHP. After a 2 hr incubation at 37° C., the cells were assayed for viability as described.

Sulindac Enhances the Killing of the SCC Skin Cancer Cell Line by Hydrogen Peroxide:

Experiments were performed with the SCC skin cancer cells that were pretreated with 500 µM sulindac and then hydrogen peroxide ($H_2O_2$) for 24 hours instead of TBHP. The data clearly show that this alternative form of oxidative stress leads to a similar enhanced cell killing when cells are pretreated with sulindac (FIG. 2).

Figure 2:
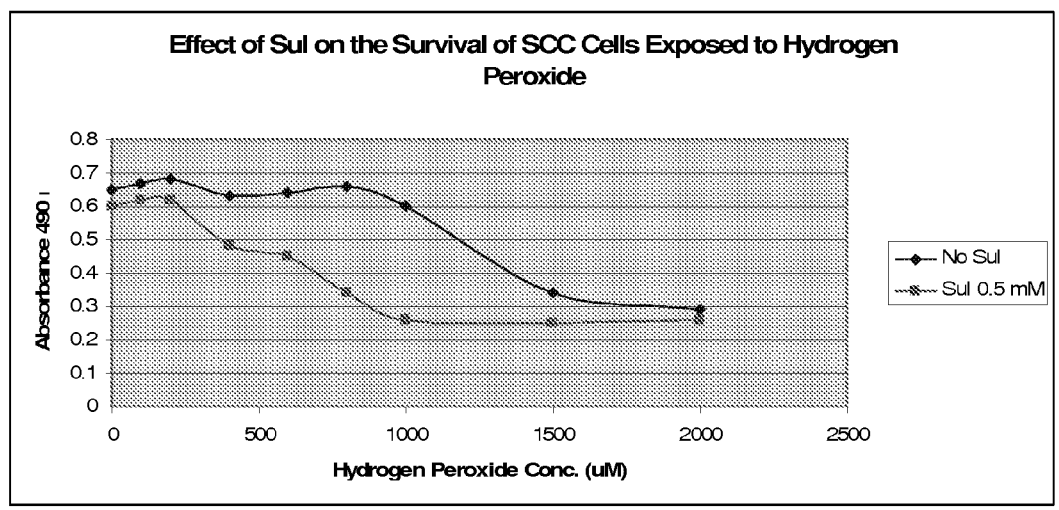
FIG. 2 is a graph showing the effect of hydrogen peroxide on viability of SCC skin cancer cells following pretreatment with 500 µM sulindac. SCC skin cancer cells were incubated for 24 hr in the presence or absence of 500 µM sulindac. The medium was removed and the cells washed once with fresh medium followed by addition of medium containing the indicated concentration of hydrogen peroxide ($H_2O_2$). After a 24 hr incubation at 37° C., the cells were assayed for viability as described in the text.

FIG. 2 shows the effect of hydrogen peroxide on viability of SCC skin cancer cells following pretreatment with 500 µM Sulindac. SCC skin cancer cells were incubated for 24 hr in the presence (♦) or absence (■) of 500 µM sulindac. The medium was removed and the cells washed once with fresh medium followed by addition of medium containing the indicated concentration of hydrogen peroxide ($H_2O_2$). After a 24 hr incubation at 37° C., the cells were assayed for viability as described.

Sulindac Enhances the Killing of the SCC Skin Cancer Cell Line by Arsenic Trioxide:

Experiments were performed with the SCC skin cancer cells that were pretreated with 500 µM sulindac but using arsenic trioxide for 24 hours instead of peroxide. Arsenic trioxide was used since it is a compound capable of giving rise to oxidative damage by a mechanism that leads to the generation of ROS inside the mitochondria. The data clearly show that this alternative form of oxidative stress leads to a similar enhanced cell killing when cells are pretreated with sulindac (FIG. 3).

Figure 3:
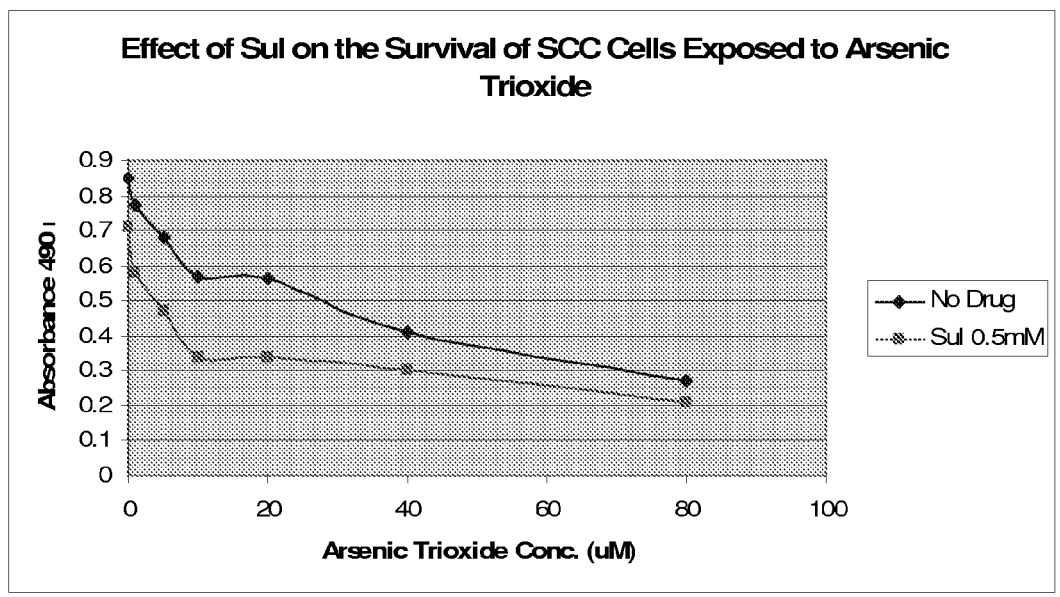
FIG. 3 is a graph showing the effect of arsenic trioxide on viability of SCC skin cancer cells following pretreatment with 500 µM sulindac. SCC skin cancer cells were incubated for 24 hr in the presence or absence of 500 µM sulindac. The medium was removed and the cells washed once with fresh medium followed by addition of medium containing the indicated concentration of arsenic trioxide. After a 24 hr incubation at 37° C., the cells were assayed for viability as described in the text.

FIG. 3 shows the effect of arsenic trioxide on viability of SCC skin cancer cells. Following Pretreatment with 500 µM Sulindac. SCC skin cancer cells were incubated for 24 hr in the presence or absence of 500 µM sulindac. The medium was removed and the cells washed once with fresh medium followed by addition of medium containing the indicated concentration of arsenic trioxide. After a 24 hr incubation at 37° C., the cells were assayed for viability as described.

Example 2

Killing of Colon Cancer Cells

Sulindac enhances the killing of the RKO colon cancer cell line by tert-butyl hydroperoxide (TBHP). RKO is a human colon carcinoma cell line developed by Michael Brattain [Brattain, 1984]. The cells were obtained from the American Type Culture Collection (ATCC #CRL-2577). The cells were maintained in minimum essential medium (Eagle) supplemented with 2 mM L-glutamine, Earle's BSS containing 1.5 g/L sodium bicarbonate, 0.1 mM non-essential amino acids, 1.0 mM sodium pyruvate and 10% fetal bovine serum.

Figure 4:
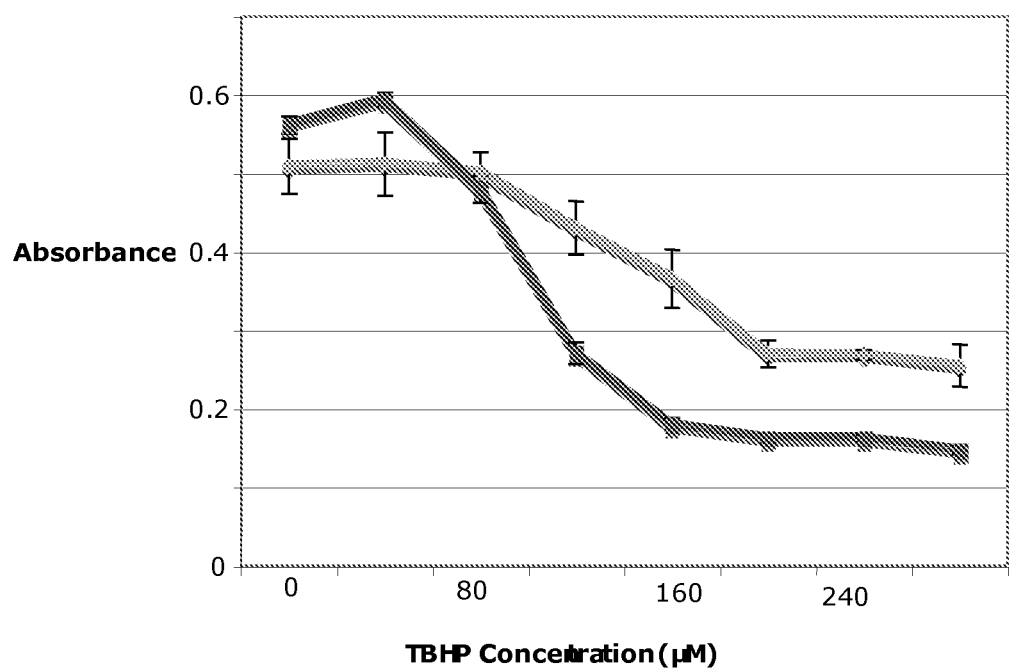
FIG. 4 is a graph showing the effect of TBHP on viability of RKO colon cancer cells following pretreatment with 500 µM sulindac. RKO colon cancer cells were incubated for 24 hr in the presence (■) or absence (♦) of 500 µM sulindac. The medium was removed and the cells washed once with fresh medium followed by addition of medium containing the indicated concentration of TBHP. After a 2 hr incubation at 37° C., the cells were assayed for viability as described in the text. Error bars represent the SEM of four replicate samples.

Experiments were performed with the RKO colon cancer cells that were pretreated with 500 µM sulindac using TBHP. The combination of pretreatment with sulindac and oxidative stress by addition of TBHP enhanced the killing of the RKO carcinoma cells (FIG. 4). The decrease in viability of RKO cells pretreated with 500 µM sulindac was statistically "very significant" ($P<0.005$) at all concentrations of TBHP from 120 µM to 300 µM, the highest concentration tested.

FIG. 4 shows the effect of TBHP on viability of RKO colon cancer cells. Following Pretreatment with 500 µM Sulindac. RKO colon cancer cells were incubated for 24 hr in the presence or absence of 500 µM sulindac. The medium was removed and the cells washed once with fresh medium followed by addition of medium containing the indicated concentration of TBHP. After a 2 hr incubation at 37° C., the cells were assayed for viability as described. Error bars represent the SEM of four replicate samples.

Sulindac Enhances the Killing of the RKO Colon Cancer Cell Line by Hydrogen Peroxide:

Experiments were performed with the RKO colon cancer cells that were pretreated with 500 µM sulindac but using hydrogen peroxide ($H_2O_2$) instead of TBHP. The data clearly show that this alternative form of oxidative stress leads to a similar enhanced cell killing when cells are pretreated with sulindac (FIG. 5).

Figure 5:
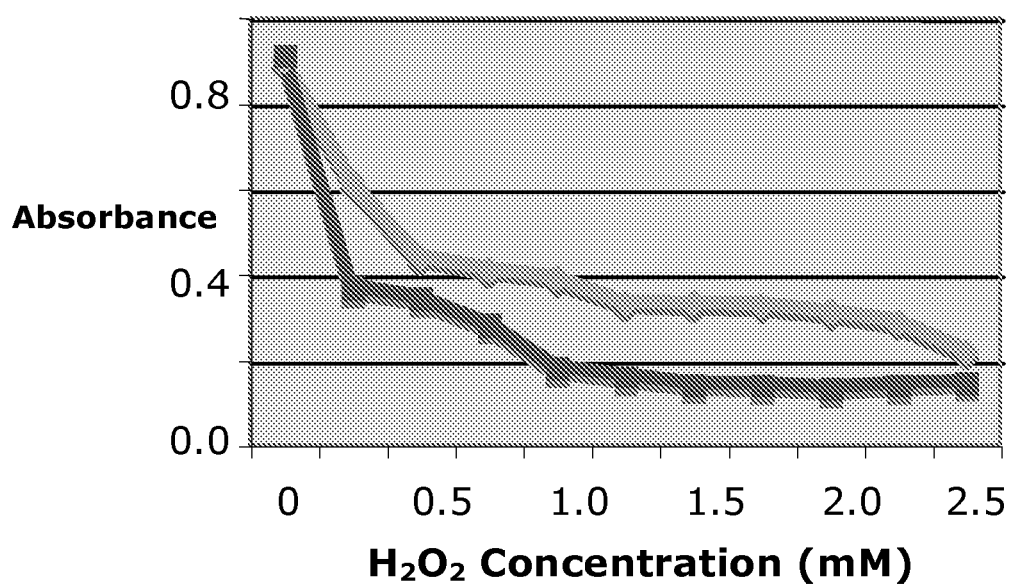
FIG. 5 is a graph showing the effect of hydrogen peroxide on viability of RKO colon cancer cells following pretreatment with 500 µM sulindac. RKO colon cancer cells were incubated for 24 hr in the presence (■) or absence (♦) of 500 µM sulindac. The medium was removed and the cells washed once with fresh medium by addition of medium containing the indicated concentration of hydrogen peroxide ($H_2O_2$). After a 2 hr incubation at 37° C., the cells were assayed for viability as described in the text.

FIG. 5 shows the effect of hydrogen peroxide on viability of RKO colon cancer cells following pretreatment with 500 µM Sulindac. RKO colon cancer cells were incubated for 24 hr in the presence or absence of 500 µM sulindac. The medium was removed and the cells washed once with fresh medium followed by addition of medium containing the indicated concentration of hydrogen peroxide ($H_2O_2$). After a 2 hr incubation at 37° C., the cells were assayed for viability as described.

Example 3

Killing of Lung Cancer Cells

Sulindac enhances the killing of a lung carcinoma cell line by TBHP. Experiments using similar methods were performed with a lung carcinoma cell line designated A549. The cell line is obtained from the American Type Culture Collection (ATCC #CCL 185). The line was established by D. J. Giard using an explant of lung carcinomatous tissue from a 58-year-old Caucasian male [Giard, 1973]. Cells were grown in Ham's F12K medium supplemented with final concentrations of 2 mM L-glutamine, 1.6 g/L sodium bicarbonate and 10% fetal bovine serum. Cultures were maintained between $6 \times 10^3$-$6 \times 10^4$ cells/$cm^2$ in standard tissue culture flasks. The protocol for pretreatment of cells with 500 µM sulindac followed by a two hour exposure to various concentrations of TBHP was the same as that described for the RKO colon cancer cells.

Figure 6:
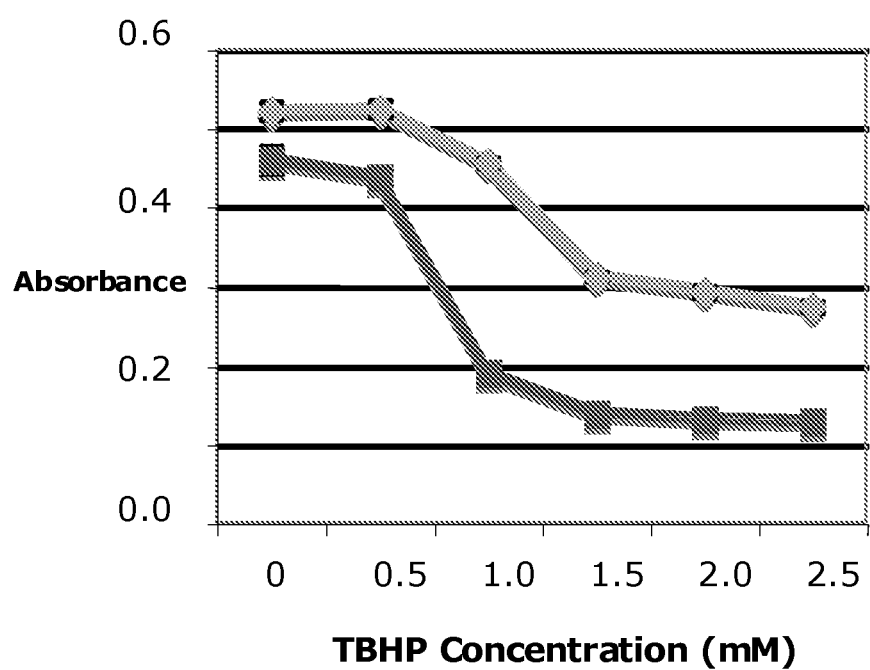
FIG. 6 is a graph showing the effect of TBHP on viability of lung cancer cells following pretreatment with 500 µM sulindac. Lung cancer cells were incubated for 24 hr in the presence (■) or absence (♦) of 500 µM sulindac. The medium was removed and the cells washed once with fresh medium followed by addition of medium containing the indicated concentration of TBHP. After a 2 hr incubation at 37° C., the cells were assayed for viability as described in the text. Error bars represent the SEM of four replicate samples.

Following a 24 hr pretreatment with 500 µM sulindac, the cells were washed once to remove the excess sulindac before exposure to TBHP for 2 hr. The lung cancer cell line also shows a marked decrease in cell viability when pretreated with 500 µM sulindac followed by exposure to TBHP (FIG. 6). Overall, the lung carcinoma cells appear to be more resistant to TBHP, so higher concentrations were used compared to the experiments with the RKO cells. At concentrations of 1 mM-2.5 mM TBHP, the difference in cell viability between control and sulindac treated cells was statistically "extremely significant" ($P<0.0001$). In the presence of 1.5-2.0 mM TBHP, approximately 50% of the untreated cells were still viable whereas viability of cells pretreated with sulindac was at background levels.

Our studies with lung cells reveal the same types of results as with the skin cells in terms of intracellular ROS levels. Lung cancer cells treated with the combination of sulindac and TBHP had significantly higher levels of ROS than with either treatment alone. The results were synergistic. Normal lung cells had lower levels of ROS with the combination.

FIG. 6 shows the effect of TBHP on viability of lung cancer cells following pretreatment with 500 µM Sulindac. Lung cancer cells were incubated for 24 hr in the presence or absence of 500 µM sulindac. The medium was removed and the cells washed once with fresh medium followed by addition of medium containing the indicated concentration of TBHP. After a 2 hr incubation at 37° C., the cells were assayed for viability as described. Error bars represent the SEM of four replicate samples.

Figure 7:
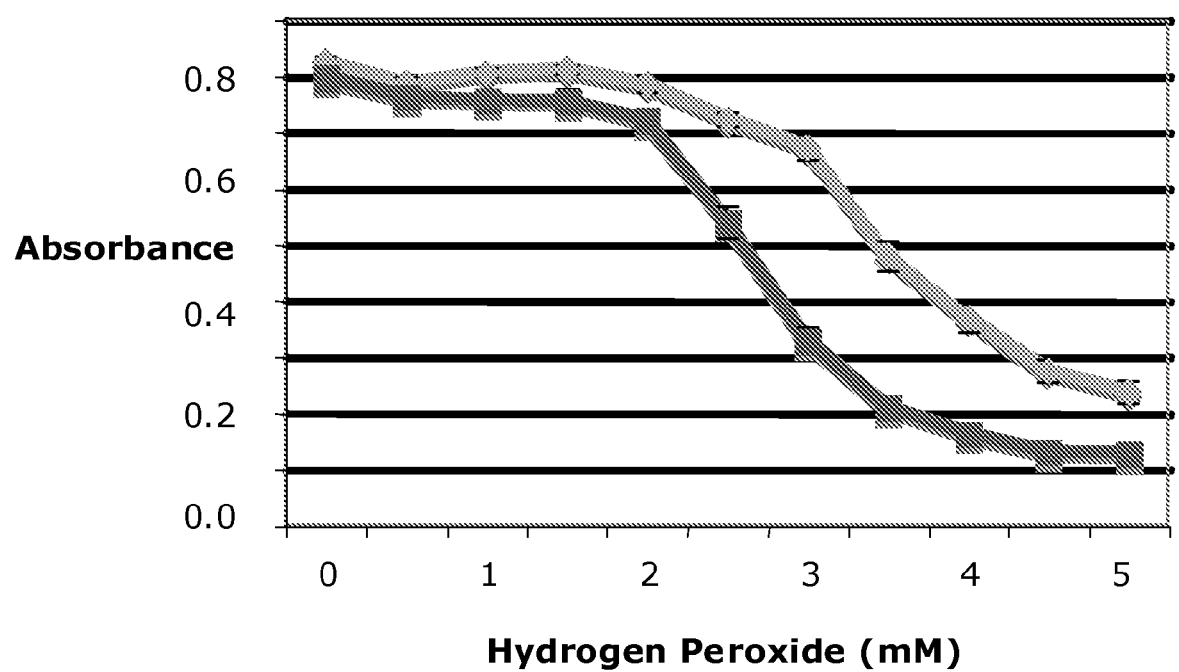
FIG. 7 is a graph showing the effect of hydrogen peroxide on viability of lung cancer cells following pretreatment with 500 µM sulindac. Lung cancer cells were incubated for 24 hr in the presence (■) or absence (♦) of 500 µM sulindac. The medium was removed and the cells washed once with fresh medium followed by addition of medium containing the indicated concentration of hydrogen peroxide. After a 2 hr incubation at 37° C., the cells were assayed for viability as described in the text. Error bars represent the SEM for replicate samples.

Sulindac Enhances the Killing of a Lung Carcinoma Cell Line by Hydrogen Peroxide:

Experiments were performed with the lung carcinoma cells using hydrogen peroxide instead of TBHP. Lung cancer cells pretreated with 500 µM sulindac are differentially sensitive to killing by $H_2O_2$ compared to untreated cells (FIG. 7). In the range of 2.5-5.0 mM $H_2O_2$, the difference in cell viability between sulindac-treated and untreated cells is statistically "highly significant" (P<0.001).

FIG. 7 shows the effect of hydrogen peroxide on viability of lung cancer cells following pretreatment with 500 µM sulindac. Lung cancer cells were incubated for 24 hr in the presence or absence of 500 µM sulindac. The medium was removed and the cells washed once with fresh medium followed by addition of medium containing the indicated concentration of hydrogen peroxide. After a 2 hr incubation at 37° C., the cells were assayed for viability as described. Error bars represent the SEM for replicate samples.

Example 4

Killing of Melanoma Cells

Sulindac enhances the killing of the human WM-266-4 Melanoma skin cell line by tert-butyl hydroperoxide (TBHP). WM-266-4 is a human melanoma cell line developed by the Wistar Institute. The cells are obtained from the American Type Culture Collection (ATCC #CRL-1676). The cells were maintained in minimum essential medium (Eagle) supplemented with 2 mM L-glutamine, Earle's BSS containing 1.5 g/L sodium bicarbonate, 0.1 mM non-essential amino acids, 1.0 mM sodium pyruvate and 10% fetal bovine serum.

Figure 8:
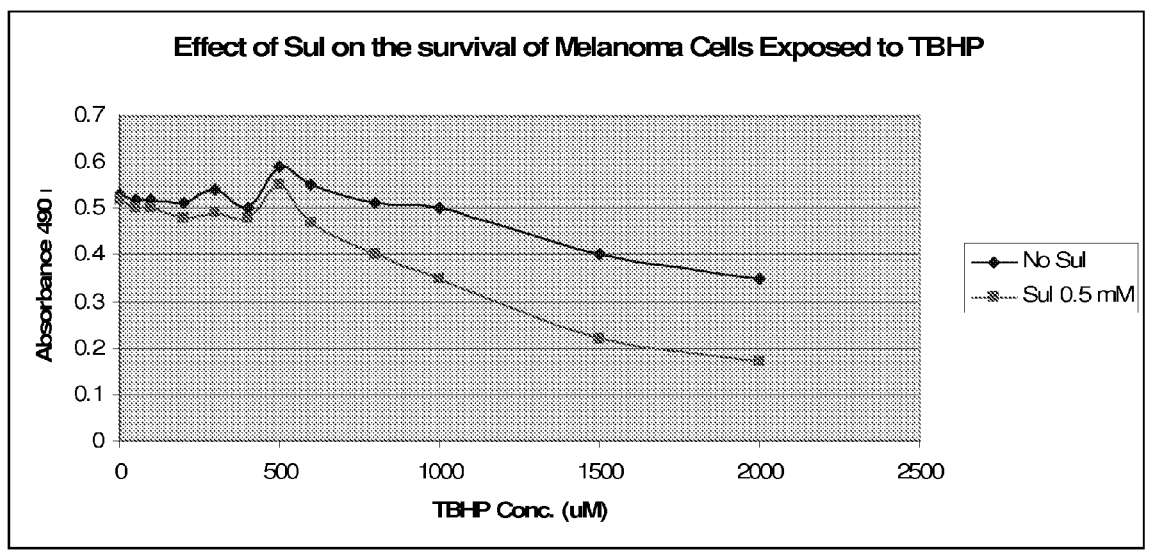
FIG. 8 is a graph showing the effect of TBHP on viability of melanoma cells following pretreatment with 500 µM sulindac. Melanoma skin cancer cells were incubated for 24 hr in the presence or absence of 500 µM sulindac. The medium was removed and the cells washed once with fresh medium followed by addition of medium containing the indicated concentration of TBHP. After a 2 hr incubation at 37° C., the cells were assayed for viability as described in the text.

Experiments were performed with the Melanoma skin cancer cells that were pretreated with 500 µM sulindac using TBHP. The combination of pretreatment with sulindac and oxidative stress by addition of TBHP enhanced the killing of the Melanoma cells (FIG. 8). The decrease in viability of Melanoma cells pretreated with 500 µM sulindac was evident at concentrations of TBHP from 600 µM to 2000 µM.

FIG. 8 shows the effect of TBHP on viability of melanoma cells following pretreatment with 500 µM Sulindac. Melanoma skin cancer cells were incubated for 24 hr in the presence or absence of 500 µM sulindac. The medium was removed and the cells washed once with fresh medium followed by addition of medium containing the indicated concentration of TBHP. After a 2 hr incubation at 37° C., the cells were assayed for viability as described.

Sulindac Enhances the Killing of the Human WM-266-4 Melanoma Skin Cell Line by Arsenic Trioxide:

Experiments were performed with the melanoma cells that were pretreated with 500 µM sulindac but using arsenic trioxide for 24 hours instead of TBHP. Arsenic trioxide was used since it is a compound capable of giving rise to oxidative damage by a mechanism that leads to the generation of elevated ROS levels inside the mitochondria. The data clearly show that this alternative form of oxidative stress leads to a similar enhanced cell killing effect when cells are pretreated with sulindac (FIG. 9).

Figure 9:
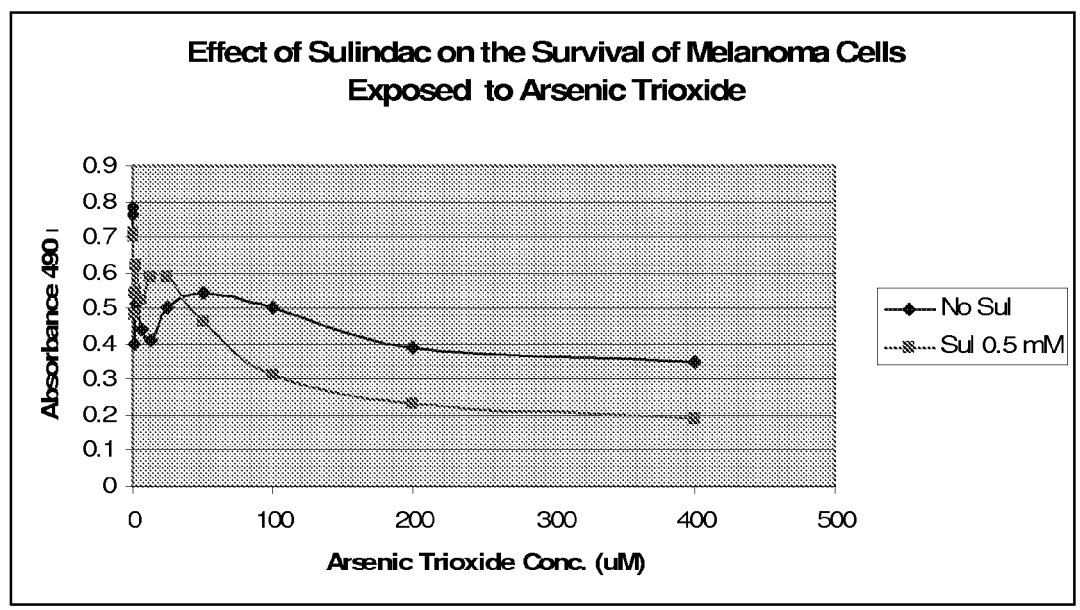
FIG. 9 is a graph effect of arsenic trioxide on viability of melanoma cells following pretreatment with 500 µM sulindac. Melanoma cells were incubated for 24 hr in the presence or absence of 500 µM sulindac. The medium was removed and the cells washed once with fresh medium followed by addition of medium containing the indicated concentration of arsenic trioxide. After a 24 hr incubation at 37° C., the cells were assayed for viability as described in the text.

FIG. 9 shows the effect of arsenic trioxide on viability of melanoma cells following pretreatment with 500 µM Sulindac. Melanoma cells were incubated for 24 hr in the presence or absence of 500 µM sulindac. The medium was removed and the cells washed once with fresh medium followed by addition of medium containing the indicated concentration of arsenic trioxide. After a 24 hr incubation at 37° C., the cells were assayed for viability as described. Sulindac does not enhance the killing of normal cells by TBHP or arsenic trioxide.

Example 5

No Effects on Normal Human Skin Cells

Experiments using similar methods were performed with primary human neonatal foreskin epidermal keratinocytes. These cells were of low-passage and purified using previously accepted protocols (provided by J. Li, University of Miami, Fl.). Cells were grown in 50% Keratinocyte-SFM media [Gibco-Invitrogen (Catalog #17005-042) supplemented with human recombinant Epidermal Growth Factor 1-53 (EGF 1-53) and Bovine Pituitary Extract (BPE)] with 50% EpiLife medium [Cascade Biologics (Catalog #Epi-500-Ca)] supplemented with purified bovine serum albumin, purified bovine transferrin, hydrocortisone, recombinant human insulin-like growth factor type-1 (rhIGF-1), prostaglandin E2 (PGE2), and recombinant human epidermal growth factor (rhEGF).

Experimental conditions: Normal HEK skin cells plated onto 6-well plates at cell density of 60-70% confluence. Sulindac (0.5 mM)×24 hours (cell density remained about the same) followed by TBHP×2 hours followed by ROS indicator dye (5 µM)×1 hour (Table 1).

TABLE 1

| % Cells with ROS Uptake by Fluorescence (fold increase compared to untreated control) | | | | |
|---|---|---|---|---|
| No Sul/No TBHP | Sul alone | Sul + TBHP (200 µM) | Sul + TBHP (400 µM) | Sul + TBHP (800 µM) |
| 3 | 2 | 3(0) | 12(4) | 68(23) |
|   |   | 2(0) | 5(2) | 60(20) |

Sulindac had no significant effect when combined with TBHP on the level of ROS uptake in normal HEK cells.

Figure 10A:
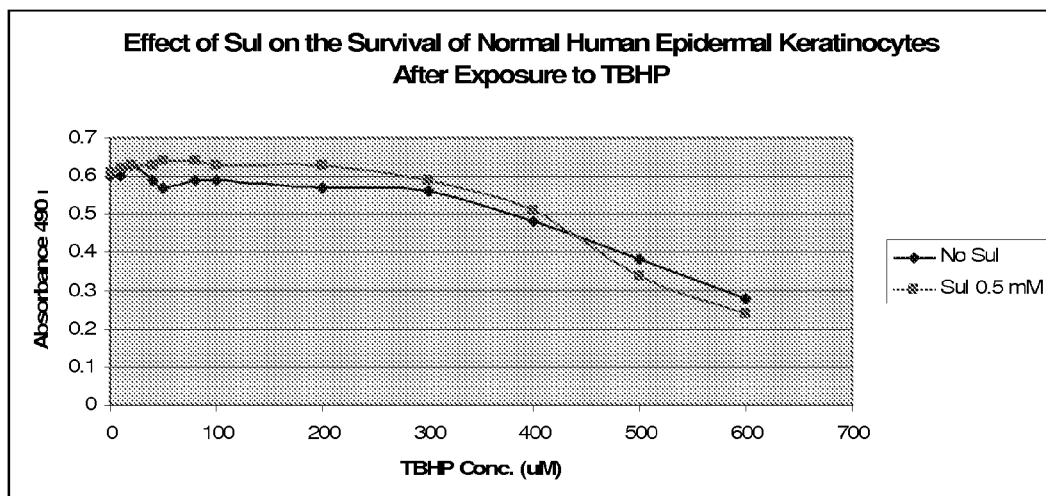
FIGS. 10A and 10B are graphs showing the effect of TBHP on viability of normal human epidermal keratinocytes following pretreatment with 500 µM sulindac. Normal human epidermal keratinocyte cells were incubated for 24 hr in the presence or absence of 500 µM sulindac. The medium was removed and the cells washed once with fresh medium followed by addition of medium containing the indicated concentration of TBHP (FIG. 10A) or arsenic trioxide (FIG. 10B). After a 2 hr incubation with TBHP or a 24-hour incubation with arsenic trioxide at 37° C., the cells were assayed for viability as described in the text.
Figure 10B:
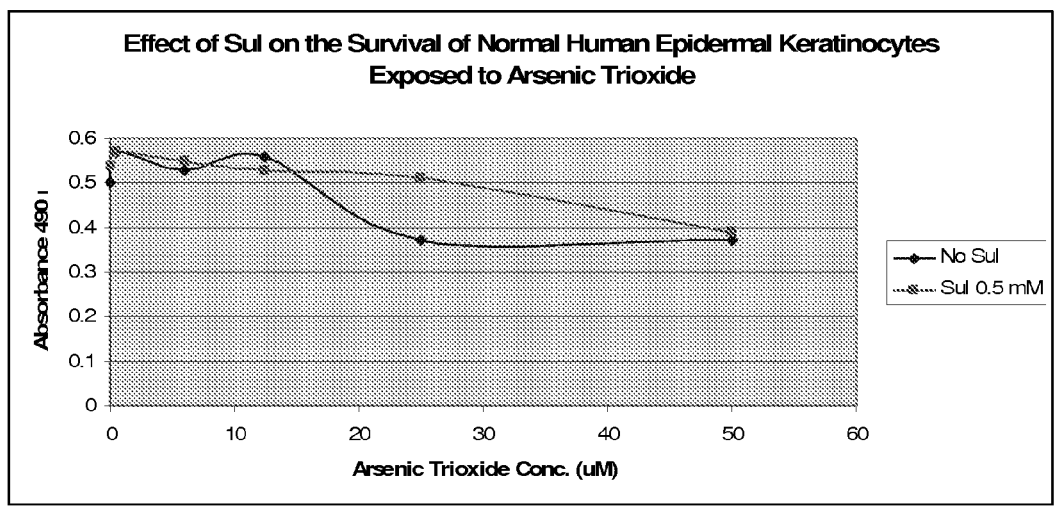

The combination of pretreatment with sulindac and oxidative stress by addition of TBHP or arsenic trioxide had no significant effect on the viability of the normal human epidermal keratinocytes (FIG. 10). A similar effect was seen with hydrogen peroxide. These results are in contrast to what was evident with the skin cancer cells (FIGS. 1-3). At the lower concentrations of TBHP (50-400 µM), in combination with sulindac, there was an enhanced resistance to oxidative stress manifested by a protective effect. This protective effect was lost at concentrations of TBHP above 400 µM.

FIG. 10 shows the effect of TBHP on viability of normal human epidermal keratinocytes following pretreatment with 500 µM Sulindac. Normal human epidermal keratinocyte cells were incubated for 24 hr in the presence or absence of 500 µM sulindac. The medium was removed and the cells washed once with fresh medium followed by addition of medium containing the indicated concentration of (a) TBHP or (b) arsenic trioxide. After a 2 hr incubation with TBHP or a 24-hour incubation with arsenic trioxide at 37° C., the cells were assayed for viability as described.

Normal Human Colon & Lung Cells:

Pretreatment of normal human colon and lung cells with sulindac provides protection from oxidative stress. CCD-18Co is a normal human colon cell line and MRC-5 is a normal human lung cell line obtained from the American Type Culture Collection (ATCC #CRL-1459 and #CCL-171). The cells were maintained in minimum essential medium (Eagle) supplemented with 2 mM L-glutamine, Earle's BSS containing 1.5 g/L sodium bicarbonate, 0.1 mM non-essential amino acids, 1.0 mM sodium pyruvate and 10% fetal bovine serum.

Experiments were performed with the normal human colon and normal human lung cells that were pretreated with 500 µM sulindac followed by the use of TBHP. The combination of pretreatment with sulindac and oxidative stress by addition of TBHP provided protection from oxidative stress. (FIGS. 11 & 12).

Figure 11:
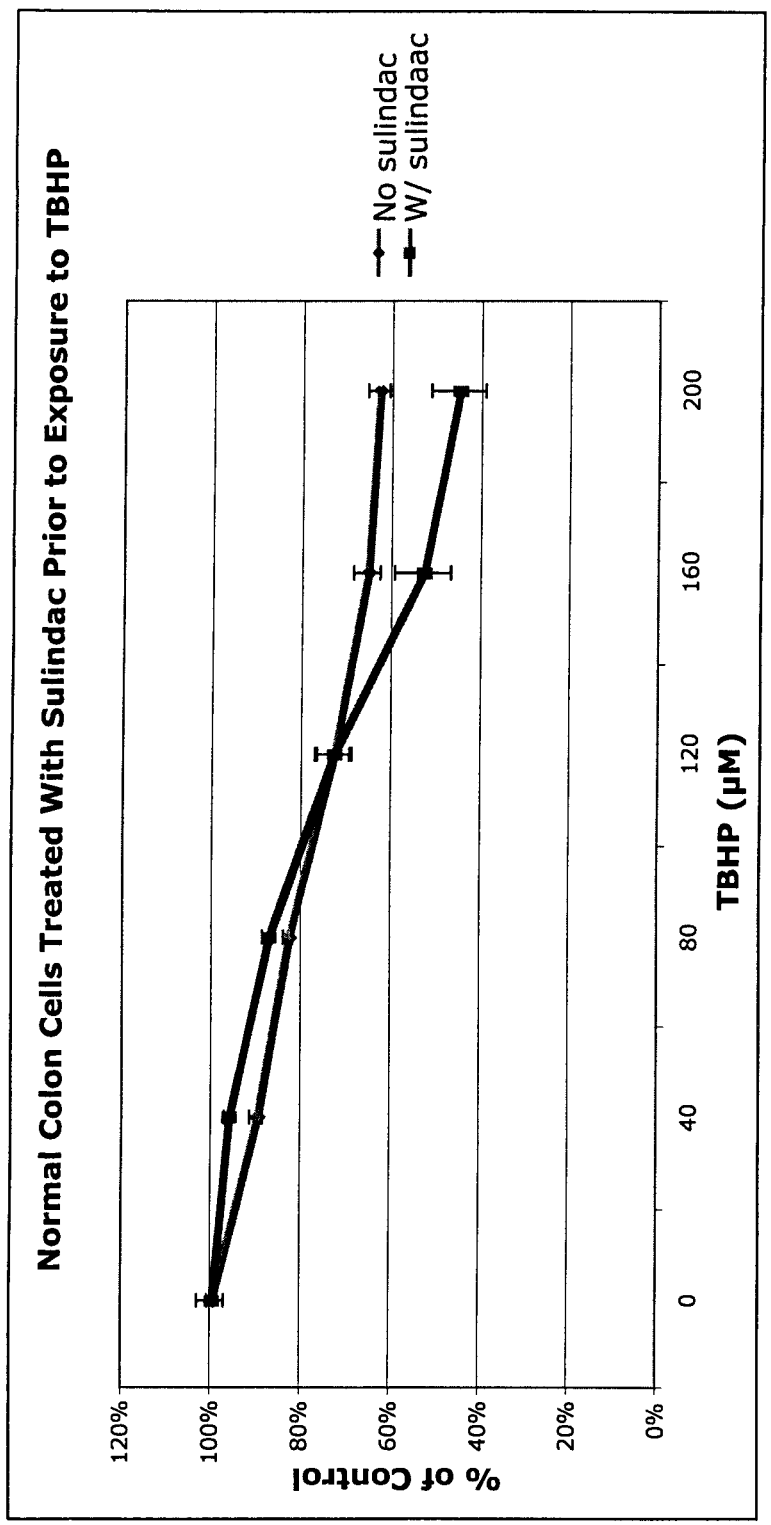
FIG. 11 is a graph showing the effect of TBHP on normal human colon cells pretreated with sulindac. Normal diploid colon cells were incubated for 24 hr with medium containing 500 µM sulindac or no addition (no sulindac). Cells were washed free of sulindac prior to incubation for 2 hr with the indicated concentration of TBHP. Cell viability was measured using the MTS assay described. Results are expressed as % of Control (cells that were not pretreated or exposed to TBHP). Error bars are standard error of the mean (SEM) expressed as a % of the mean value of four replicate samples.

FIG. 11 shows the effect of TBHP on normal human colon cells pretreated with sulindac. Normal diploid colon cells were incubated for 24 hr with medium containing 500 µM sulindac or no addition (no sulindac). Cells were washed free of sulindac prior to incubation for 2 hr with the indicated concentration of TBHP. Cell viability was measured using the MTS assay. Results are expressed as % of Control (cells that were not pretreated or exposed to TBHP). Error bars are standard error of the mean (SEM) expressed as a % of the mean value of four replicate samples.

Figure 12:
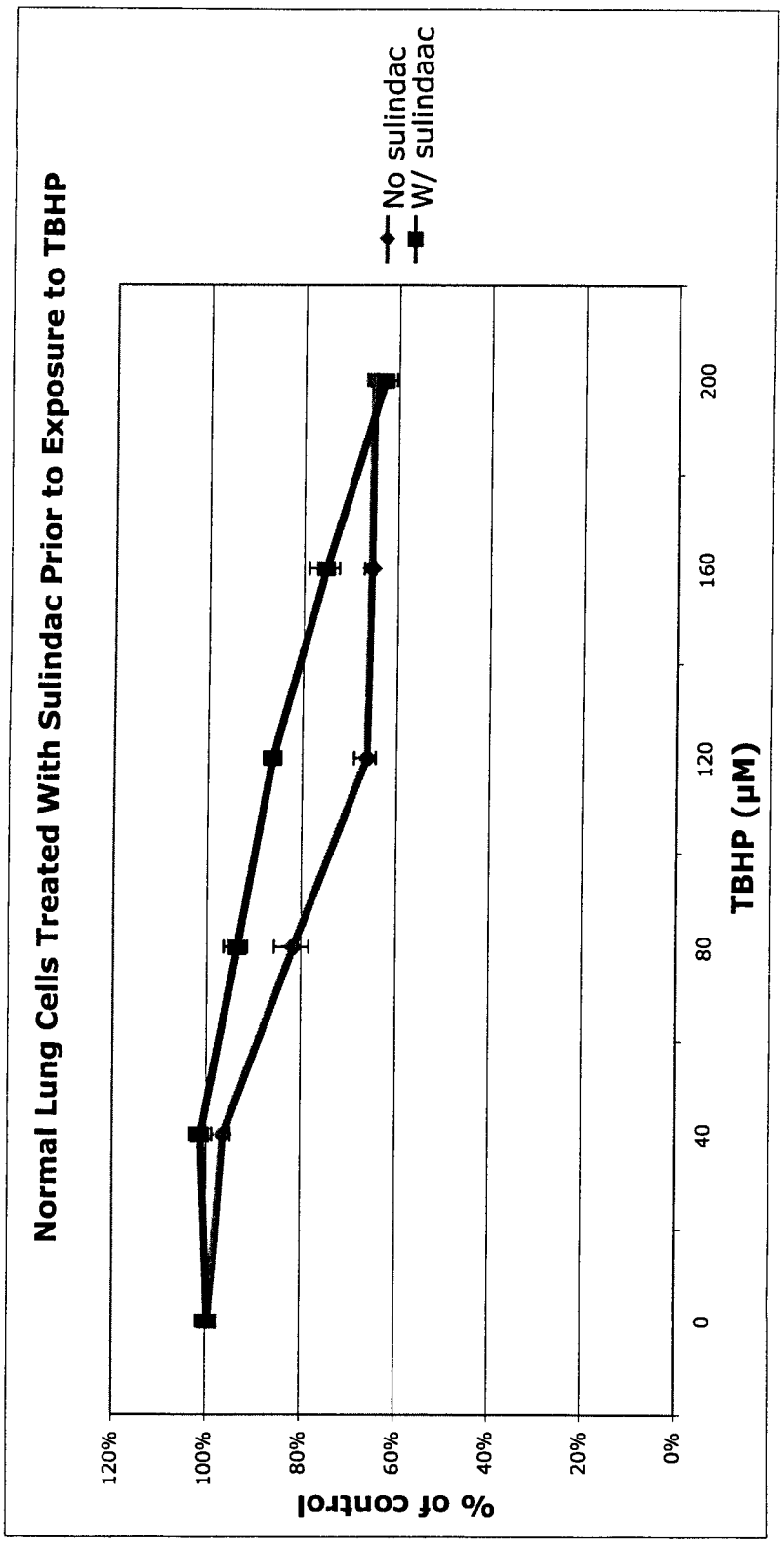
FIG. 12 is a graph showing the effect of TBHP on normal human lung cells pretreated with sulindac. Normal diploid lung cells were incubated for 24 hr with medium containing 500 µM sulindac or no addition (no sulindac). Cells were washed free of sulindac prior to incubation for 2 hr with the indicated concentration of TBHP. Cell viability was measured using the MTS assay. Results are expressed as % of Control (cells that were not pretreated or exposed to TBHP). Error bars are standard error of the mean (SEM) expressed as a % of the mean value of four replicate samples.

FIG. 12 shows the effect of TBHP on normal human lung cells pretreated with sulindac. Normal diploid lung cells were incubated for 24 hr with medium containing 500 µM sulindac or no addition (no sulindac). Cells were washed free of sulindac prior to incubation for 2 hr with the indicated concentration of TBHP. Cell viability was measured using the MTS assay described. Results are expressed as % of Control (cells that were not pretreated or exposed to TBHP). Error bars are standard error of the mean (SEM) expressed as a % of the mean value of four replicate samples.

In sharp contrast to the results obtained with the transformed cells, each of the three normal human cell lines (skin, colon, and lung) showed enhanced resistance to oxidative stress when pretreated with sulindac for 24 hr.

Normal Cardiac & Retinal Cells:

Sulindac does not enhance the killing of normal cardiac and retinal cells by hydrogen peroxide and TBHP. Primary neonatal rat cardiac myocytes and ARPE-19, a human retinal pigment epithelial cell line that is not fully transformed, were used in similar experiments with sulindac followed by peroxide. The results showed that there was no enhanced killing of these normal cells using the combination of sulindac and peroxide.

Figure 16:
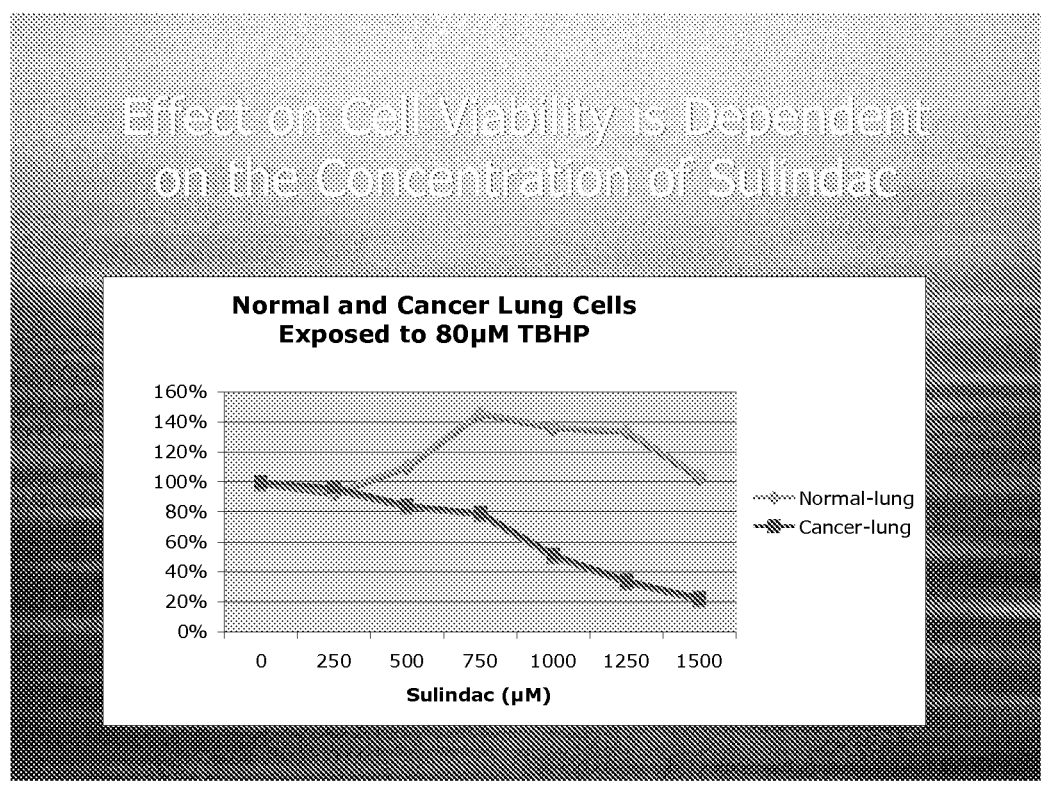
FIG. 16 is a graph showing a constant non-toxic TBHP concentration in combination with escalating doses of sulindac, the effects on normal vs. cancer cells can be better elucidated. There is a protective effect on normal cells while an enhanced killing of cancer cells occurs. In this experiment, the gap or difference in cell survival widens between the cell types over a 3-5× concentration range of sulindac (500 µM-1500 µM).

FIG. 16 shows that at a constant non-toxic TBHP concentration in combination with escalating doses of sulindac, the effects on normal versus cancer cells can be better elucidated. There is a protective effect on normal cells while an enhanced killing of cancer cells occurs.

In this experiment, the gap or difference in cell survival widens between the cell types over a 3-5× concentration range of sulindac (500 µM-1500 µM).

Example 6

Sulindac Metabolites/Derivatives

Figures 13A, 13B, 13C, 13D:
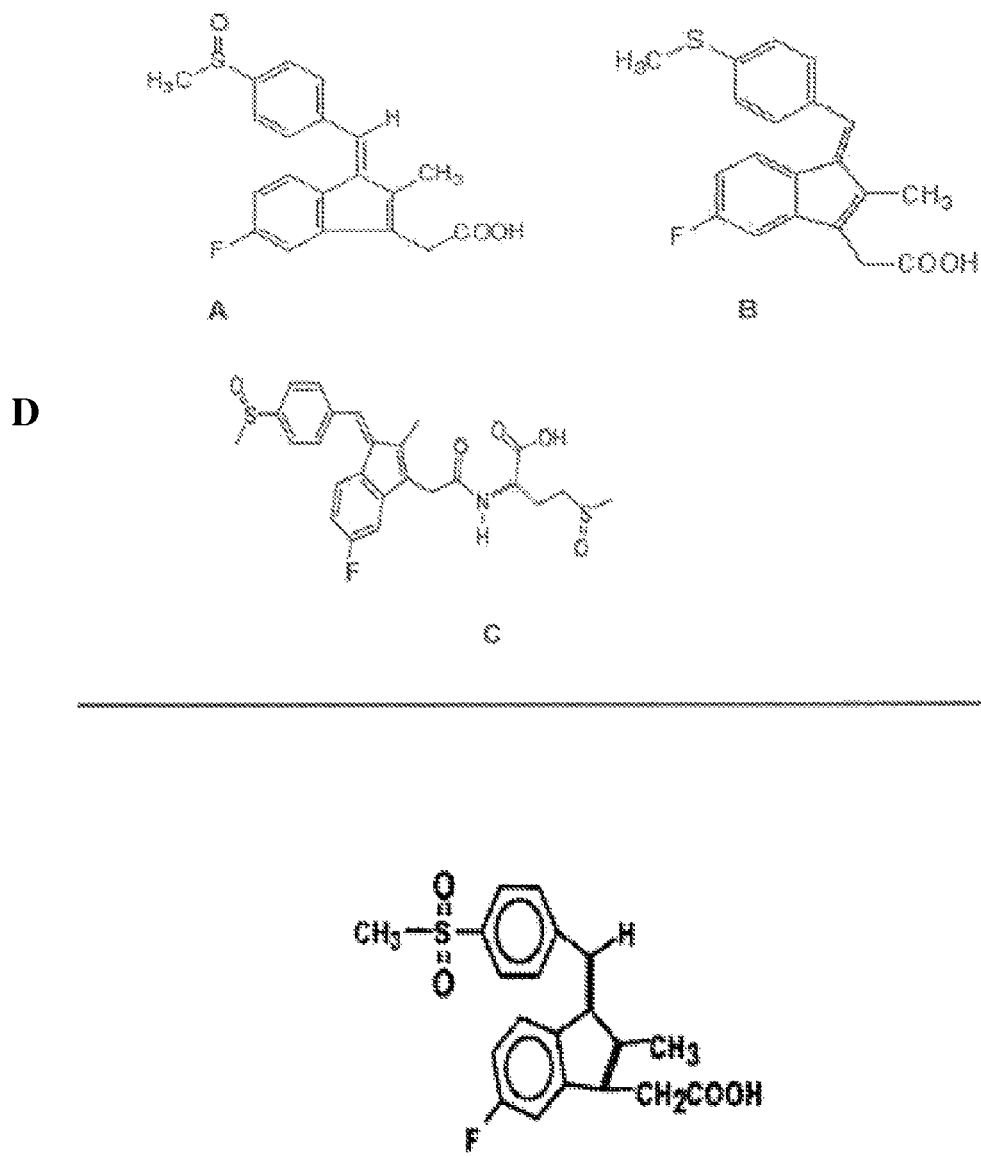
FIGS. 13A-D shows the structures of (FIG. 13A) Sulindac (FIG. 13B) Sulindac Sulfide (FIG. 13C) Sulindac Methionine Sulfoxide and D) Sulindac Sulfone.
Figure 14:
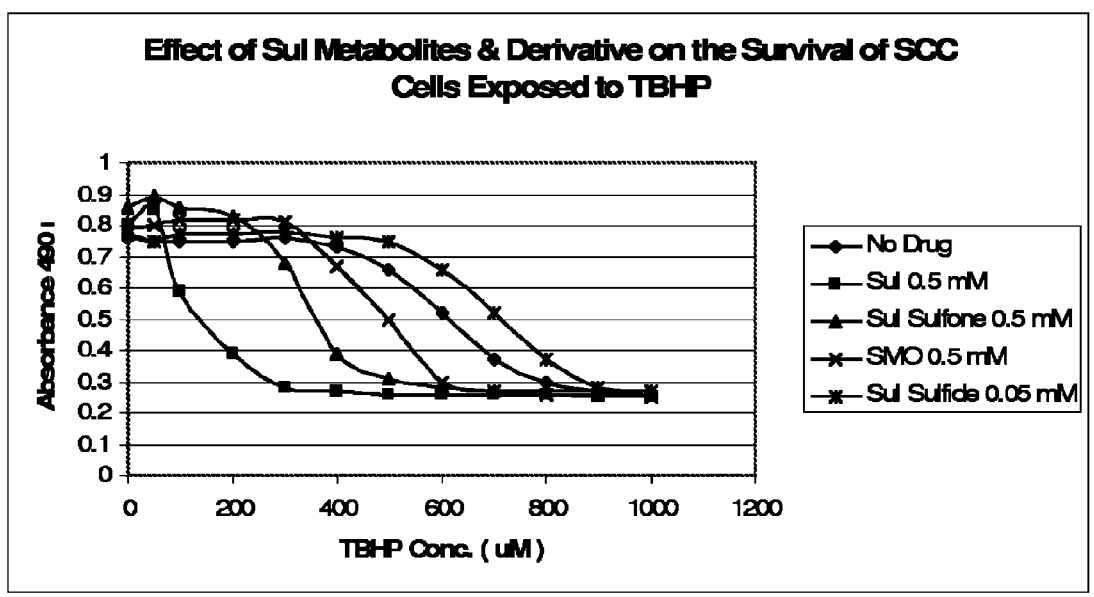
FIG. 14 is a graph showing skin cancer cells treated with sulindac, sulindac metabolites, or a sulindac derivative. Skin cancer cells were incubated for 24 hr with medium containing 500 µM sulindac, 500 µM sulindac sulfone, 500 µM SMO, 50 µM sulindac sulfide or no addition (no pretreatment). Cells were washed free of compound prior to incubation for 2 hr with the indicated concentration of TBHP. Cell viability was measured using the MTS assay.

A sulindac metabolite enhances the killing of cancer cells by TBHP. The structure of sulindac and its metabolites and a derivative, sulindac methionine sulfoxide (SMO), are shown in FIG. 13. A metabolite of sulindac, specifically sulindac sulfone, was effective in enhancing the killing of skin cancer cells (SCC-25) when exposed to TBHP (FIG. 14). Sulindac was more potent than the sulfone metabolite. The SMO derivative and the other metabolite of sulindac, specifically sulindac sulfide, were not effective in enhancing the killing of the skin cancer cells when exposed to TBHP.

However, when lung cancer cells or melanoma cells were exposed to TBHP, the sulindac sulfide metabolite had activity in reducing the cell viability. In summary, in all cancer cell studies, sulindac and sulindac sulfone had the most potent killing effect (FIG. 15).

FIG. 14 shows the results from skin cancer cells treated with sulindac, sulindac metabolites, or a sulindac derivative. Skin cancer cells were incubated for 24 hr with medium containing 500 µM sulindac, 500 µM sulindac sulfone, 500 µM SMO, 50 µM sulindac sulfide or no addition (no pretreatment). Cells were washed free of compound prior to incubation for 2 hr with the indicated concentration of TBHP. Cell viability was measured using the MTS assay described.

Figure 15:
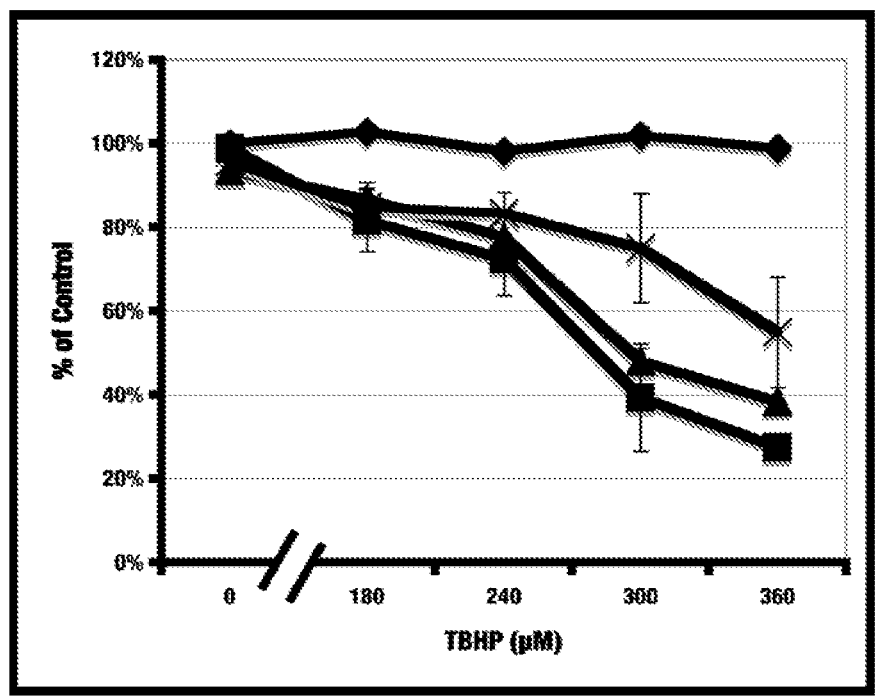
FIG. 15 is a graph showing the effect of sulindac and its metabolites on the viability of lung cancer cells in response to oxidative stress. Lung cancer cells were incubated for 24 hr with medium containing 500 µM sulindac (■), 250 µM sulindac sulfone (▲), 250 µM sulindac sulfide ( ) or no addition (♦). For all concentrations of TBHP tested, $p<0.05$.

FIG. 15 shows lung cancer cells treated with sulindac or its metabolites. Lung cancer cells were incubated for 24 hr with medium containing 500 µM sulindac, 250 µM sulindac sulfone, 250 µM sulindac sulfide or no addition (no pretreatment). Cells were washed free of sulindac prior to incubation for 2 hr with the indicated concentration of TBHP. Cell viability was measured using the MTS assay. Results are expressed as % of Control (cells that were not pretreated or exposed to TBHP). Error bars are standard error of the mean (SEM) expressed as a % of the mean value of four replicate samples.

Other Experiments:

SCC skin cancer cells plated onto 6-well plates at cell density of 50-60% confluence. Sulindac (0.5 mM)×24 hours (cell density increased to 80-90% confluence) followed by TBHP (100 µM)×2 hours followed by ROS indicator dye (5 µM)×1 hour (Table 2).

TABLE 2

| Experimental Condition | % Cells with ROS Uptake by Fluorescence | fold increase compared to untreated control |
|---|---|---|
| NO Sul/NO TBHP | 1.6% | — |
| Sul alone | 3% | 2 |
| TBHP alone | 11% | 7 |
| Sul + TBHP | 30% | 19 |

Conclusion

Sulindac enhances the levels of ROS uptake in SCC skin cancer cells. Sulindac in combination with TBHP geometrically enhances the levels of ROS uptake. Sulindac tends to increase the number of spindle cells in the culture compared to untreated controls Other NSAIDS do not enhance the killing of the SCC-25 skin cancer cells or RKO colon carcinoma cell line by TBHP. Acetylsalicylic acid, ibuprofen, diclofenac sodium, and celecoxib at comparable active concentrations, were found to be ineffective compared to sulindac in sensitizing the skin cancer cells and or colon cancer cells to killing by TBHP.

Sulindac in combination with an oxidizing agent increases the intracellular levels of ROS in cancer cells. SCC skin cancer cells were plated onto 6-well plates at a cell density of 50-60% confluence. The cultures were pretreated with sulindac (500 uM) for 24 hours followed by the addition of TBHP (100 uM) for two hours. During this period of time, the cell density in the 6-well plates increased to 80-90% confluent. This was immediately followed by the addition of the ROS indicator dye [(5 uM) Carboxy-H2DCFDA (5-(and 6-)carboxy-2',7'-dichlorodihydrofluorescein diacetate, Molecular Probes, Carlsbad, Calif.] for one hour. The cancer cells were visually inspected using a fluorescence microscope and counted. Cells with green fluorescence were considered to have an increased level of ROS. Sulindac and TBHP both enhanced the ROS levels in SCC cells (Table 3). Sulindac in combination with TBHP synergistically enhanced the ROS levels in skin cancer cells (2× the additive value of sulindac or TBHP alone).

TABLE 3

| Treatment | % Cells containing ROS* | fold increase (compared to untreated control) |
|---|---|---|
| NO Sul/NO TBHP | 1.6 | — |
| Sul (500 μM) alone | 3 | 2 |
| TBHP (100 μM) alone | 11 | 7 |
| Sul (500 μM) + TBHP (100 μM) | 30 | 19 |

*ROS levels were measured by green fluorescence observed using a fluorescence microscope.

Sulindac in combination with an oxidizing agent has no effect on the intracellular levels of ROS in normal skin cells. Human neonatal epidermal keratinocytes were plated into 6-well plates at a cell density of 60-70% confluence. The cultures were pretreated with sulindac (500 uM) for 34 hours followed by the addition of different concentrations of TBHP for 2 hours. During this period of time, the cell density in the 6-well plates remained the same (there was no increase in cell proliferation). This was followed by the addition of the ROS indicator dye. Sulindac when combined with TBHP had no significant effect over what was seen with sulindac or TBHP alone on the ROS levels in normal human skin cells (Table 4).

TABLE 4

| Treatment | % Cells containing ROS* (fold increase compared to untreated control) |
|---|---|
| No Sul/No TBHP | 3 (0) |
| Sul (500 uM) alone | 2 (0) |
| TBHP (200 uM) alone | 2 (0) |
| TBHP (400 uM) alone | 5 (2) |
| TBHP (800 uM) alone | 60 (20) |
| Sul (500 uM) + TBHP (200 uM) | 3 (0) |
| Sul (500 uM) + TBHP (400 uM) | 12 (4) |
| Sul (500 uM) + TBHP (800 uM) | 68 (23) |

ROS levels were measured by green fluorescence observed using a fluorescence microscope Additional Information on the Experiments with Sulindac and the ROS Generators (Hydrogen Peroxide, TBHP and Arsenic):

Sulindac was pre-incubated for various times prior to the addition of the oxidant. Time course studies revealed that it was necessary for the sulindac to be pre-incubated for a minimum of 6 hours to see an effect. Optimum effects were seen with an 18-24 hour incubation. There was no difference in the results with longer time courses such as 48-72 hours. After the pre-incubation with sulindac, the cells were washed and the oxidant was added with or without sulindac.

TBHP experiments were performed using 2 hour incubations with no additional sulindac.

Hydrogen peroxide and arsenic trioxide experiments were performed with 24 hour incubations with the re-addition of sulindac.

Patients with precancerous growths and BCC's exhibited a beneficial response to a topical formulation of a composition of sulindac and hydrogen peroxide. A few drops of a topical formulation of 5% or 10% sulindac gel was administered once or twice a day for up to 4 weeks to several patients over skin areas that had precancerous growths and/or BCC's. After 10-15 minutes, this application was followed by the application of several drops of hydrogen peroxide solution (6%-25%) for 5-10 minutes once or twice a day. In each instance, after 2-5 days, the patients exhibited some minimal swelling and redness with mild irritation to the involved areas not seen on normal adjacent skin. A bright yellowish hue was localized on the growths that seemed to be most intense on the overlying scale. After 4 weeks of treatment, a number of precancerous growths were visibly diminished in size or gone. The BCC's looked much smaller in size and, in certain locations, were no longer visible. There has been no recurrence of the growths that have visibly disappeared in the areas of treatment after 6 months. The patients are continued to be followed for an evaluation of their long-term responses.

Example 7

Treatment of Patient with Actinic Keratoses

A male patient had a number of scaly growths (actinic keratoses), on the face. Four areas were selected for treatment, including one on his temple with a large scale crust. After continuous treatment with the 5% sulindac gel formulation, in combination with 6% hydrogen peroxide solution at least once a day for 4 weeks, the patient had a complete response. All four actinic keratoses resolved and disappeared, including the one with the large scale. There has been no recurrence in the areas of the treated growths after 6 months of observation.

Example 8

Treatment of Patient with Basal Cell Carcinoma

A male in his mid to late 50's had recurrent basal cell carcinoma on the right temple and right forehead. Doctors recommended their removal by Moh's surgery. However, the surgery could have led to unacceptable cosmetic results with scarring. After continuous treatment with 10% sulindac gel formulation in combination with 12% hydrogen peroxide solution, for at least once a day for 10 weeks, the patient had a complete response. Both skin cancers are not visible after 3 months of follow-up. (See, FIGS. 17 and 18).

Figure 17:
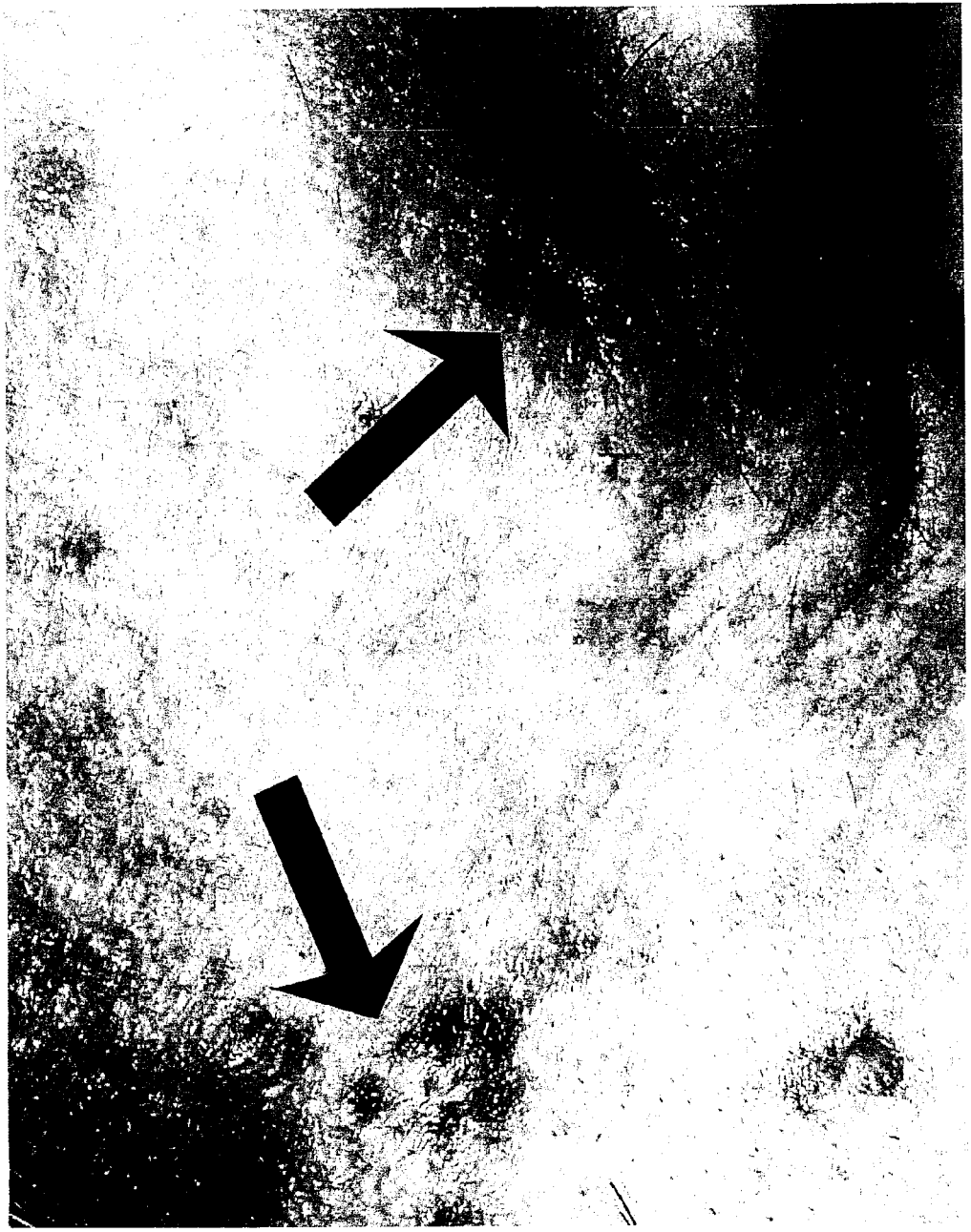
FIG. 17 is a scan of a photograph showing basal cell carcinomas before treatment with sulindac peroxide. The black arrows point to two recurrent basal cell carcinomas on the face of a patient. A 0.5 centimeter ulcerated area with pearly irregular borders on the right forehead near the right upper eyelid and a 1.5 centimeter poorly circumscribed lesion with pearly ill-defined nodular borders on the right temple area near the hairline.

FIG. 17 is a scan of a photograph showing basal cell carcinomas before treatment with sulindac peroxide. The black arrows point to two recurrent basal cell carcinomas on the face of a patient. A 0.5 centimeter ulcerated area with pearly irregular borders on the right forehead near the right upper eyelid and a 1.5 centimeter poorly circumscribed lesion with pearly ill-defined nodular borders on the right temple area near the hairline.

Figure 18:
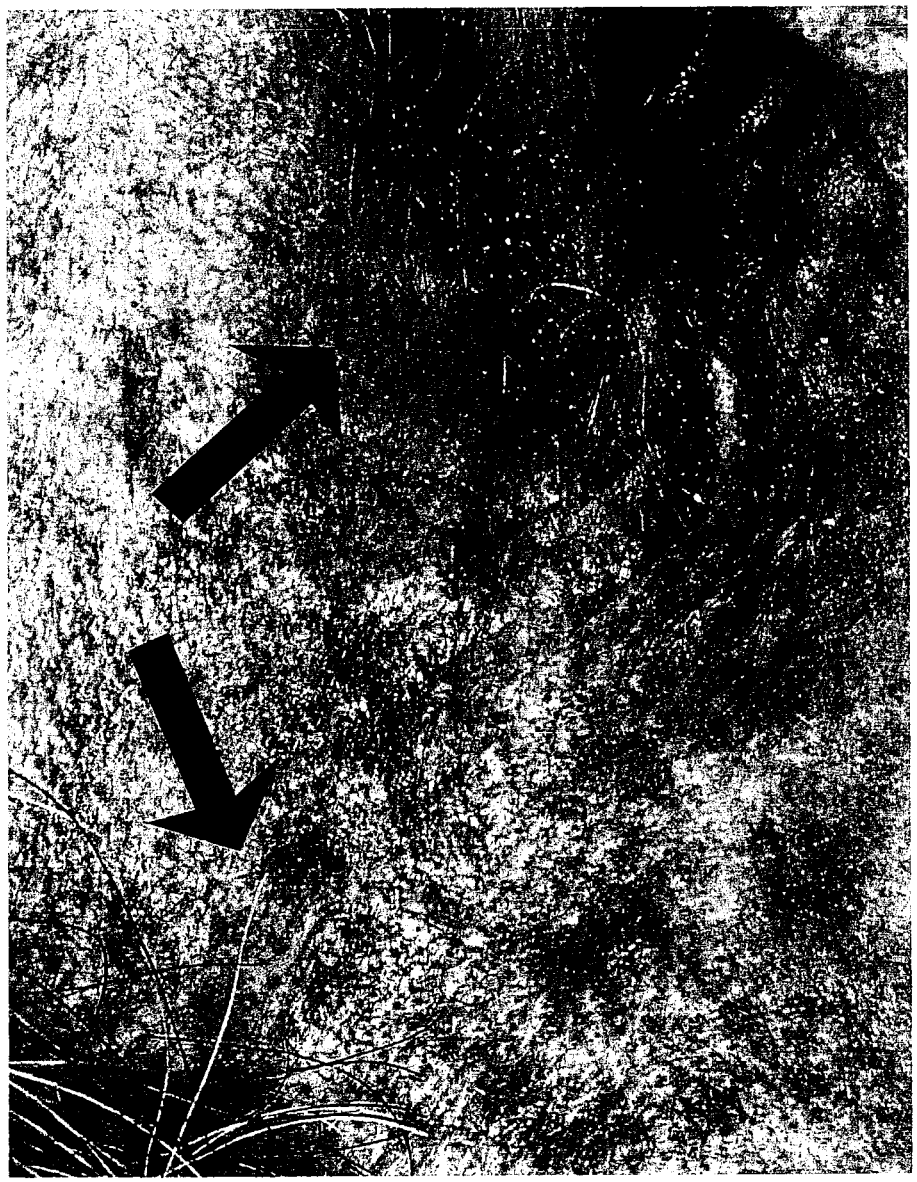
FIG. 18 is a scan of a photograph showing the basal cell carcinomas of FIG. 17, after treatment with sulindac peroxide. The black arrows point to the two areas on the skin of the face that previously contained biopsy proven recurrent basal cell skin cancers (as described in FIG. 17) showing the disappearance of the cancers after treatment with sulindac-peroxide formulations. The areas have healed with small amounts of scar tissue present.

FIG. 18 is a scan of a photograph showing the basal cell carcinomas of FIG. 17, after treatment with sulindac peroxide. The black arrows point to the two areas on the skin of the face that previously contained biopsy proven recurrent basal cell skin cancers (as described in FIG. 17) showing the disappearance of the cancers after treatment with sulindac-peroxide formulations. The areas have healed with small amounts of scar tissue present.

Example 9

Treatment of Patient with Squamous Cell Carcinoma

A male in his 60's had a non-healing large scaly growth on his right hand. It was a biopsy proven hypertrophic actinic keratosis. The growth had been treated with liquid nitrogen three times over the previous year without success. On visual inspection, the growth could have represented a superficial squamous cell carcinoma. After the application of the topical 10% sulindac gel in combination with 25% hydrogen peroxide solution (Table 5), for at least once a day for 6 weeks, the patient had a complete response. (See, FIGS. 19 and 20). The growth has not recurred after 3 months of follow-up).

Figure 19:
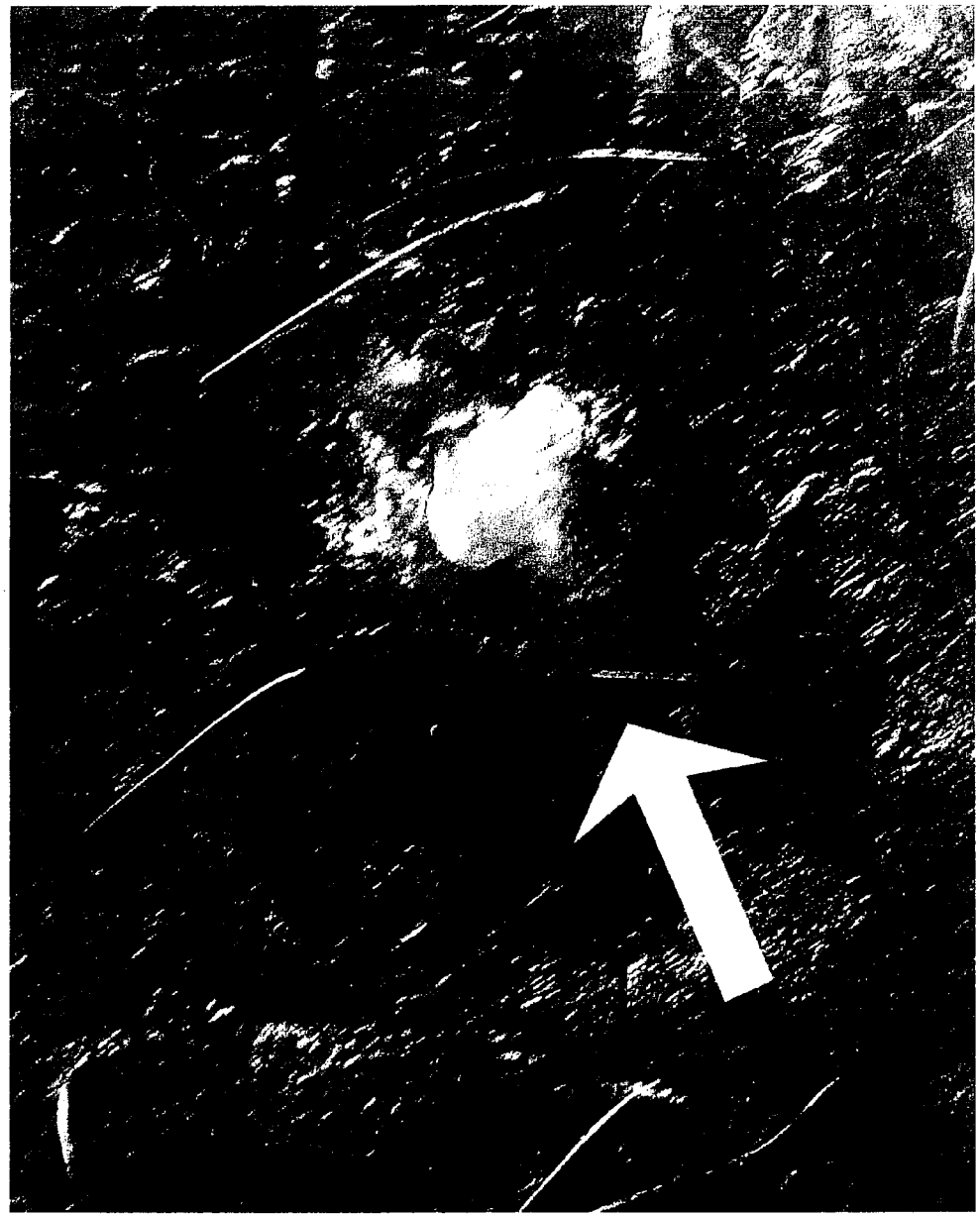
FIG. 19 is a scan of a photograph showing a hyperkeratotic lesion before treatment with the sulindac-peroxide formulation. The white arrow points to a 1 centimeter hyperkeratotic lesion on the right hand representing a hypertrophic actinic keratosis or squamous cell carcinoma before treatment with sulindac-peroxide formulations.

FIG. 19 is a scan of a photograph showing a hyperkeratotic lesion before treatment with the sulindac-peroxide formulation. The white arrow points to a 1 centimeter hyperkeratotic lesion on the right hand representing a hypertrophic actinic keratosis or squamous cell carcinoma before treatment with sulindac-peroxide formulations.

Figure 20:
FIG. 20 is a scan of a photograph showing the hyperkeratotic lesion after treatment with sulindac-peroxide of the same patient in FIG. 19. The white arrow points to the area of previous skin lesion (as described in FIG. 19) showing the eradication of the condition after treatment with the sulindac-peroxide formulations. Only a small amount of scar tissue with minimal scaling remains.

FIG. 20 is a scan of a photograph showing the hyperkeratotic lesion after treatment with sulindac-peroxide of the same patient in FIG. 19. The white arrow points to the area of previous skin lesion (as described in FIG. 19) showing the eradication of the condition after treatment with the sulindac-peroxide formulations. Only a small amount of scar tissue with minimal scaling remains.

TABLE 5

Formulation of topical 5% sulindac gel.

| Ingredient | % |
| --- | --- |
| Deionized water | 71.08 |
| SD Alcohol 40 | 12.00 |
| KOH | 10.00 |
| Sulindac | 5.00 |
| Hydroxy methyl cellulose | 1.00 |
| Xantham gum | 0.50 |
| Glydant Plus | 0.20 |
| Citric Acid | 0.20 |
| Disodium EDTA | 0.02 |

This base formula is used for 10% sulindac gels, 20% sulindac gels, 50% sulindac gels. Variations of the formula are easily adapted by one of ordinary skill in the art.

Pre-Clinical Experience in Human Patients:

Sulindac gel and hydrogen peroxide gel or liquid were applied using calibrated dropper bottles directly on the skin of volunteers with actinic keratoses. Sulindac was generally applied first although in a few instances, the peroxide was applied first. The sulindac was applied and allowed to dry for 5-10 minutes followed by the application of the peroxide. The products were not washed off the skin until after 8-12 hours of applications. Products were applied twice a day to each individual area.

Example 10

R- and S-Epimers

Figure 22:
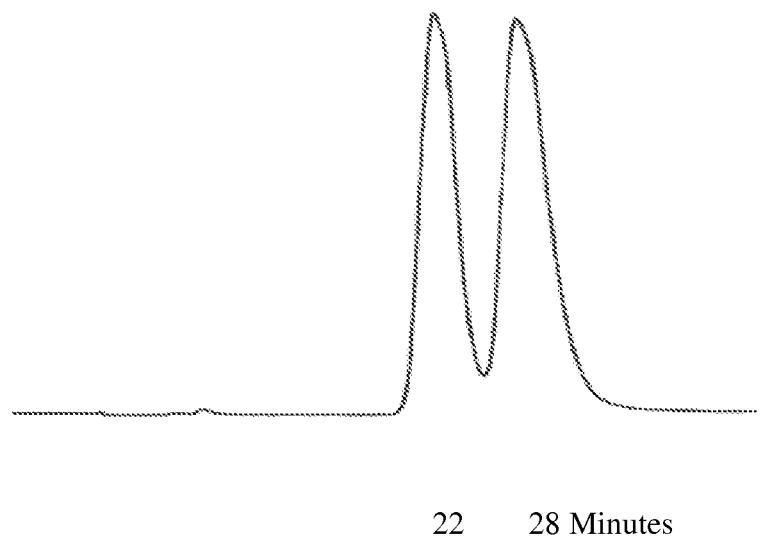
FIG. 22 is a chromatogram showing the separation of the R&S-epimers of sulindac using a chiral column. Sulindac (7 mg/ml) was dissolved in a mixture of hexane/ethanol (65/35) containing 0.1% acetic acid and 75 µl of this solution applied to the chiral column. The column was developed with the above solvent at a flow rate of 1.5 ml/min and 300 µl fractions collected. The elution of the sulindac was followed by monitoring the optical density at 256 nm. Two peaks are observed eluting after 22.5 and 28 minutes (OD 256). The R-form elutes first (22.5 min) followed by the S-form (28 min).

The R- and S-epimers of sulindac can be separated using chiral columns and HPLC. The sulindac epimers were separated and isolated from the racemic mixture with scale-up of sufficient quantities for our studies using a preparative chiral column. The chiral column (R, R)-Welk-01 chiral column (25 cm×4.6 mm) was purchased from Regis Technologies (Milton Grove, Ill.). As shown in FIG. 22, the 2 epimers of sulindac were separated quite well, under the conditions described in the legend of FIG. 22. Two peaks were observed eluting after 22.5 and 28 min. The peak tubes were combined and the solvent evaporated. The separated epimers were then dissolved in 1M Tris Cl pH 7.4. In order to determine which epimer was present in each peak, the material in each peak was incubated with *Escherichia coli* MsrA and 15 mM DTT, which would convert the S-epimer to sulindac sulfide. At the end of the incubation, the reduced product was extracted into benzene and the optical density read at 350 nm as previously described (Etienne F, Resnick L, Sagher D, Brot N, Weissbach H. *Biochem Biophys Res Comm*. 2003; 312:1005-10). It was determined that the peak eluting at 28 minutes was the S-epimer of sulindac.

The R-Epimer of Sulindac is Poorly Converted to the Sulfide (COX Inhibitor) in Whole Normal Cells as Compared to the S-Epimer:

The individual sulindac epimers were evaluated for their conversion to the sulfide in cultured whole normal cells, employing an assay developed in this laboratory (Etienne F, Resnick L, Sagher D, Brot N, Weissbach H. *Biochem Biophys Res Comm*. 2003; 312:1005-10). Enriched cultures of neonatal rat cardiac myocytes were obtained from 1-2 day-old neonatal rats by stepwise trypsin dissociation and plated at a density of 104 cells/60 mm dish in DMEM supplemented with 5% fetal calf serum, penicillin, and streptomycin. After 3-5 days, the cells were transferred to a defined serum-free DMEM/M-199 (4:1) medium supplemented with transferring, vitamin B12 and insulin. The final cultures contained greater than 97% cardiac myocytes contracting at greater than 200 beats per minute. To inhibit fibroblast growth, 0.1 mM bromodeoxyuridine was included in the medium for the first 3-5 days after plating. Cell cultures are incubated with sulindac or its individual epimers for specified times.

After the incubations, the cells were pelleted by low speed centrifugation and lysed by the addition of 200 µl of 100% acetonitrile, followed by vigorous vortexing. The lysate was centrifuged for 15 minutes at 14,000×g to pellet cell debris. 50 µl of the supernatant was transferred to an HPLC autosampler microvial. The separation of metabolites is carried out on a 4.6×75 mm C18 reverse-phase column. An isocratic flow of 1 ml/min consisting of 50% 50 mM sodium acetate, pH 4.73 and 50% acetonitrile was utilized. The metabolites are detected at a wavelength of 330 nm. With the Waters model 2487 detector, pmole quantities of the sulfide can be detected.

Figure 23:
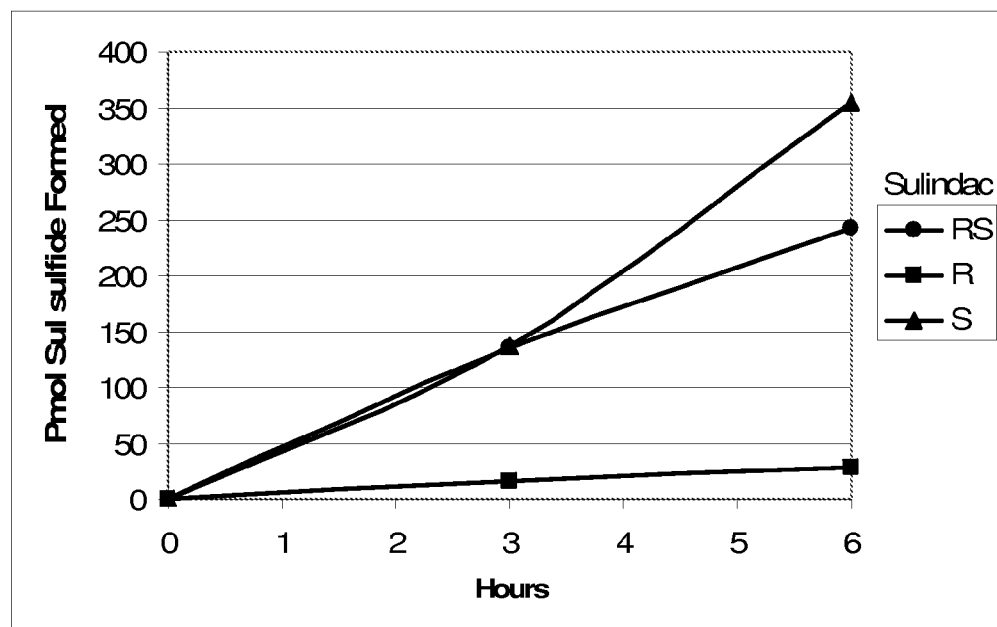
FIG. 23 is a graph showing the metabolic conversion of the R & S epimers of sulindac to the sulfide form in cardiac myocytes. The amount of sulindac sulfide formed by $10^6$ cells incubated with 400 µM sulindac, R, S or RS mixture is measured as a function of time of incubation. The assay was performed by HPLC separation of cell lysates, using a C18 column and a mobile phase of 50/50% 50 mM sodium acetate, pH 4.73, and acetonitrile. The absorbance was measured at 330 nm.

As shown in FIG. 23, in normal cardiac myocytes, the R-epimer of sulindac was very poorly converted to the sulfide (greater than 10-fold less conversion) compared to the S-epimer, under the conditions described in the legend.

Table 6 below, shows that two normal cell lines (lung and cardiomyocytes) do not reduce the R epimer as efficiently as the S epimer (<10% R/S). However, in 3 cancer cell lines (Lung, HeLa, and skin SCC), there is an enhanced conversion of the R-epimer (greater than 40%), unlike that found in normal cells (less than 10%). A significant reduction of the R-epimer of sulindac, although not seen in normal cells, has been observed in some malignant cells.

The cells are incubated with 200 µM R- or S-Sulindac epimer for 4 hours in a defined, serum-free medium (EX-CELL$^{SM}$). After incubation, the cells are collected, rinsed and lysed with acetonitrile. The cytosolic contents are separated on a C-18 column.

TABLE 6

| Cell | Amount Formed (picomoles) | | R/S (%) |
| --- | --- | --- | --- |
| | R-epimer | S-epimer | |
| Cancer | | | |
| Lung | 7.5 | 17.7 | 42 |
| HeLa | 9.3 | 7.9 | 118 |
| Skin | 35.3 | 57 | 62 |

TABLE 6-continued

| | Amount Formed (picomoles) | | |
|---|---|---|---|
| Cell | R-epimer | S-epimer | R/S (%) |
| Normal | | | |
| Lung | 2.2 | 35 | 6 |
| Cardiomyocyte | 11.6 | 120.9 | 9 |

Figure 24:
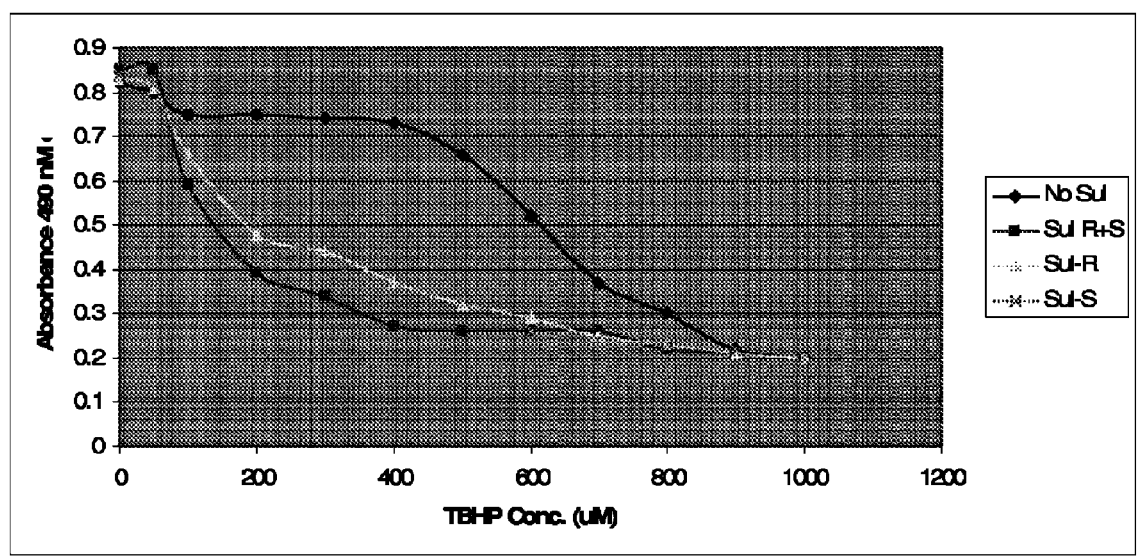
FIG. 24 is a graph showing the effect of R- & S-sulindac epimers on the killing of SCC cells after exposure to TBHP. SCC skin cancer cells were incubated for 24 hr in the presence or absence of 500 µM sulindac or 500 µM sulindac-R or -S epimers. The medium was removed and the cells washed once with fresh medium followed by addition of medium containing the indicated concentration of TBHP. After a 2 hr incubation at 37° C., the cells were assayed for viability as described in the text.
Figure 25:
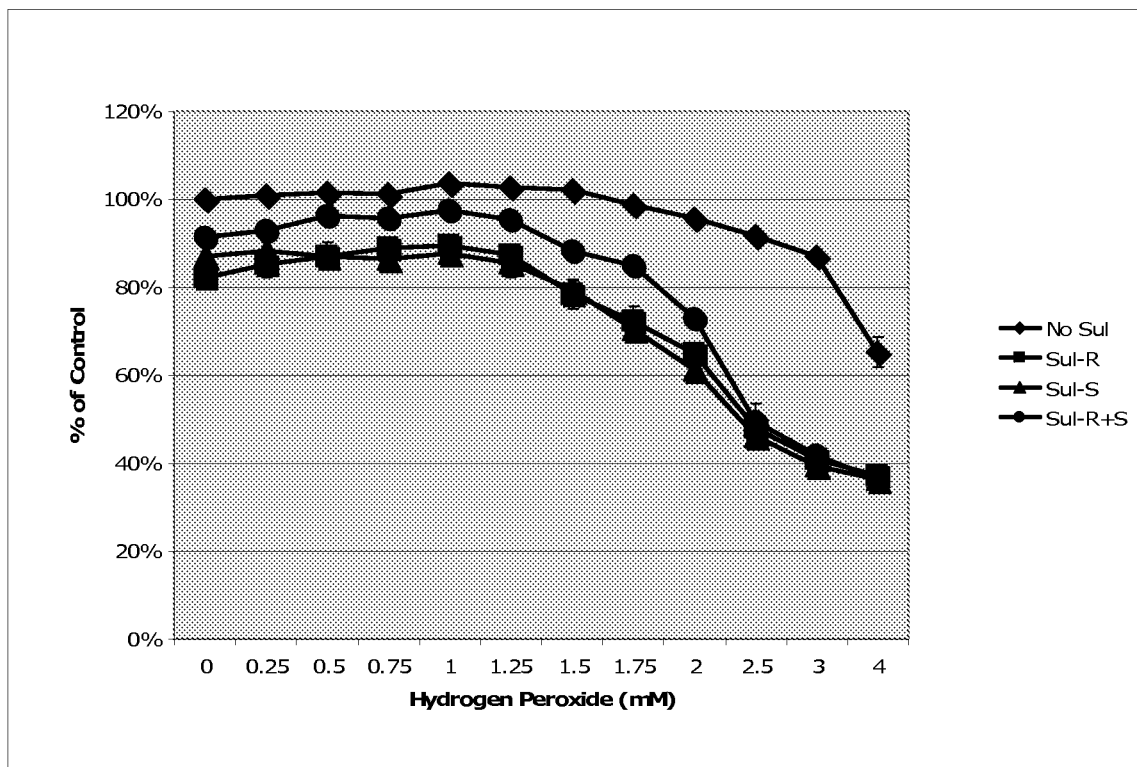
FIG. 25 is a graph showing the effect of R- & S-sulindac epimers on the killing of lung cancer cells after exposure to hydrogen peroxide. Lung cancer cells were treated with 500 µM Sulindac-R, 500 µM Sulindac-S or 500 µM Sulindac-(R+S) for 24 hours. The cells were washed free of the sulindac before incubation for 24-hrs with the indicated concentration of hydrogen peroxide. Cell viability was measured using the MTS assay as described in the text. The error bars are the SEM for four replicate samples.
Figure 26:
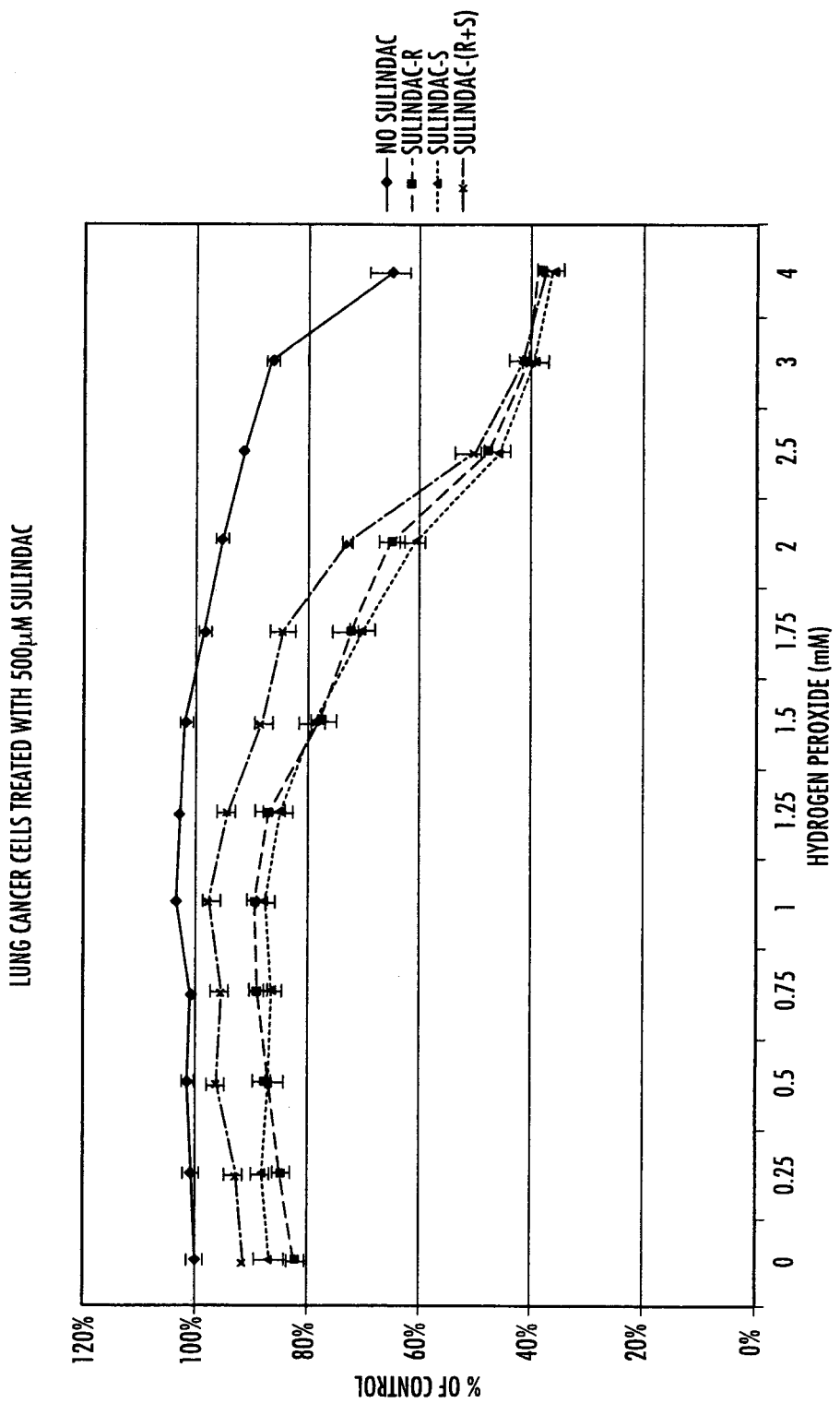
FIG. 26 is a graph showing lung cancer cells treated with 500 µM sulindac-R, 500 µM sulindac-S or 500 µM sulindac-(R+S) for 24 hr. The cells were then washed free of the sulindac before exposure to hydrogen peroxide over a range of 0-4 mM. Viability was measured by the MTS assay. Enhanced killing of the cancer cells is over the range of 1.5-3.0 mM hydrogen peroxide.

The R- and S-Epimers of Sulindac Enhance the Killing of SCC Skin and Lung Cancer Cells by TBHP or Hydrogen Peroxide:

Milligram quantities of each epimer were isolated (as shown in FIG. 22) and tested for their ability to selectively kill cancer cells. The SCC skin cancer cells or lung cancer cells were pretreated with 500 µM sulindac or 500 µM R-sulindac or 500 µM S-sulindac for 24 hours followed by the addition of TBHP for 2 hours (or hydrogen peroxide for 24-hours). The combination of pretreatment with sulindac or its individual epimers and oxidative stress enhanced the killing of the SCC and lung carcinoma cells. As shown in FIGS. 24 and 25, both epimers of sulindac had cancer killing effects that were comparable in potency to the sulindac racemic mixture. These results indicate that the R-epimer of sulindac has the potential of selectively killing cancer cells. Since in normal cells, but not cancer cells, the R-epimer of sulindac is not efficiently converted to the sulfide, the active COX inhibitor, it would be expected that normal cells would have a lower toxicity profile.

We have used a chiral column to separate the two epimers of sulindac and have evidence for the identification of the resolved HPLC peaks. The R-epimer of sulindac retains its ability to selectively kill cancer cells, while showing little or no conversion in whole normal cells to the sulfide (COX inhibitor). These results indicate that the R-epimer of sulindac has biochemical and pharmacological properties that would make it a better therapeutic agent than the unresolved sulindac-R, S mixture.

Other Embodiments

It is to be understood that while the invention has been described in conjunction with the detailed description thereof, the foregoing description is intended to illustrate and not limit the scope of the invention, which is defined by the scope of the appended claims.

What is claimed is:

1. A method for making a cancer cell more susceptible to being killed by an oxidating agent, the method comprising the step of: contacting the cancer cell with an amount of a pharmaceutical composition comprising a single epimer of sulindac that has been purified from racemic sulindac, wherein the single epimer is the R-epimer of sulindac and wherein the amount of the pharmaceutical composition is sufficient to render the cancer cell more susceptible to killing by the oxidating agent compared to the same type of cancer cell that was not contacted with the pharmaceutical composition.

2. The method of claim 1, wherein the R-epimer of sulindac is the only active ingredient in the pharmaceutical formulation.

3. The method of claim 1, wherein the cancer cell is a skin cancer cell.

4. The method of claim 1, wherein the cancer cell is a lung cancer cell.

5. The method of claim 1, further comprising the step of exposing the cancer cell that has been contacted with the pharmaceutical composition to an oxidating agent.

6. The method of claim 5, wherein the oxidating agent is a peroxide.

7. The method of claim 6, wherein the peroxide is hydrogen peroxide.

* * * * *